United States Patent
Baer

(10) Patent No.: US 7,394,077 B2
(45) Date of Patent: *Jul. 1, 2008

(54) SUPERRESOLUTION IN MICROLITHOGRAPHY AND FLUORESCENCE MICROSCOPY

(76) Inventor: Stephen C. Baer, 10 Poplar Rd., Cambridge, MA (US) 02138

( * ) Notice: Subject to any disclaimer, the term of this patent is extended or adjusted under 35 U.S.C. 154(b) by 0 days.

This patent is subject to a terminal disclaimer.

(21) Appl. No.: 11/480,672

(22) Filed: Jul. 3, 2006

(65) Prior Publication Data

US 2006/0250688 A1 Nov. 9, 2006

Related U.S. Application Data

(63) Continuation of application No. 11/147,792, filed on Jun. 7, 2005, now Pat. No. 7,071,477, which is a continuation of application No. 09/902,902, filed on Jul. 9, 2001, now Pat. No. 6,903,347, which is a continuation of application No. 09/343,054, filed on Jun. 28, 1999, now Pat. No. 6,259,104, which is a continuation of application No. 08/919,382, filed on Aug. 28, 1997, now Pat. No. 5,952,668, which is a continuation of application No. 08/581,185, filed on Dec. 29, 1995, now Pat. No. 5,777,342, which is a continuation of application No. 08/275,967, filed on Jul. 15, 1994, now Pat. No. 5,866,911.

(51) Int. Cl.
    *G01N 21/64* (2006.01)
(52) U.S. Cl. .................................. 250/458.1
(58) Field of Classification Search .............. 250/458.1
    See application file for complete search history.

(56) References Cited

U.S. PATENT DOCUMENTS

| 5,304,810 A | * | 4/1994 | Amos | 250/458.1 |
| 5,512,490 A | * | 4/1996 | Walt et al. | 436/171 |

* cited by examiner

*Primary Examiner*—Constantine Hannaher
(74) *Attorney, Agent, or Firm*—Duane Morris LLP

(57) ABSTRACT

In scanned optical systems such as confocal laser microscopes wherein a beam of light is focused to a spot in a specimen to excite a fluorescent species or other excitable species in the spot, the effective size of the excitation is made smaller than the size of the spot by providing a beam of light of wavelength adapted to quench the excitation of the excitable species, shaping this second beam into a pattern with a central intensity minimum, and overlapping this central minimum with the central intensity maximum of the focused spot, so that within the spot the intensity of quenching light increases with distance from the center of the spot, thereby preferentially quenching excitation in the peripheral parts of the spot, and thereby reducing the effective size of the excitation and thus improving the resolution of the system. In the preferred embodiment of the preset invention, the central minimum of quenching light is narrowed further by creating the pattern of quenching radiation in the specimen by imaging onto the focal plane a plurality of pairs of sources of quenching light, arrayed at the vertices of a regular, even-sided polygon, the center of which is imaged in the specimen on the central maximum of exciting radiation, and such that the two members of each pair are on opposite vertices of the polygon and emit light mutually coherent and out-of-phase, and the light emitted by different pairs is incoherent with respect to each other.

1 Claim, 16 Drawing Sheets

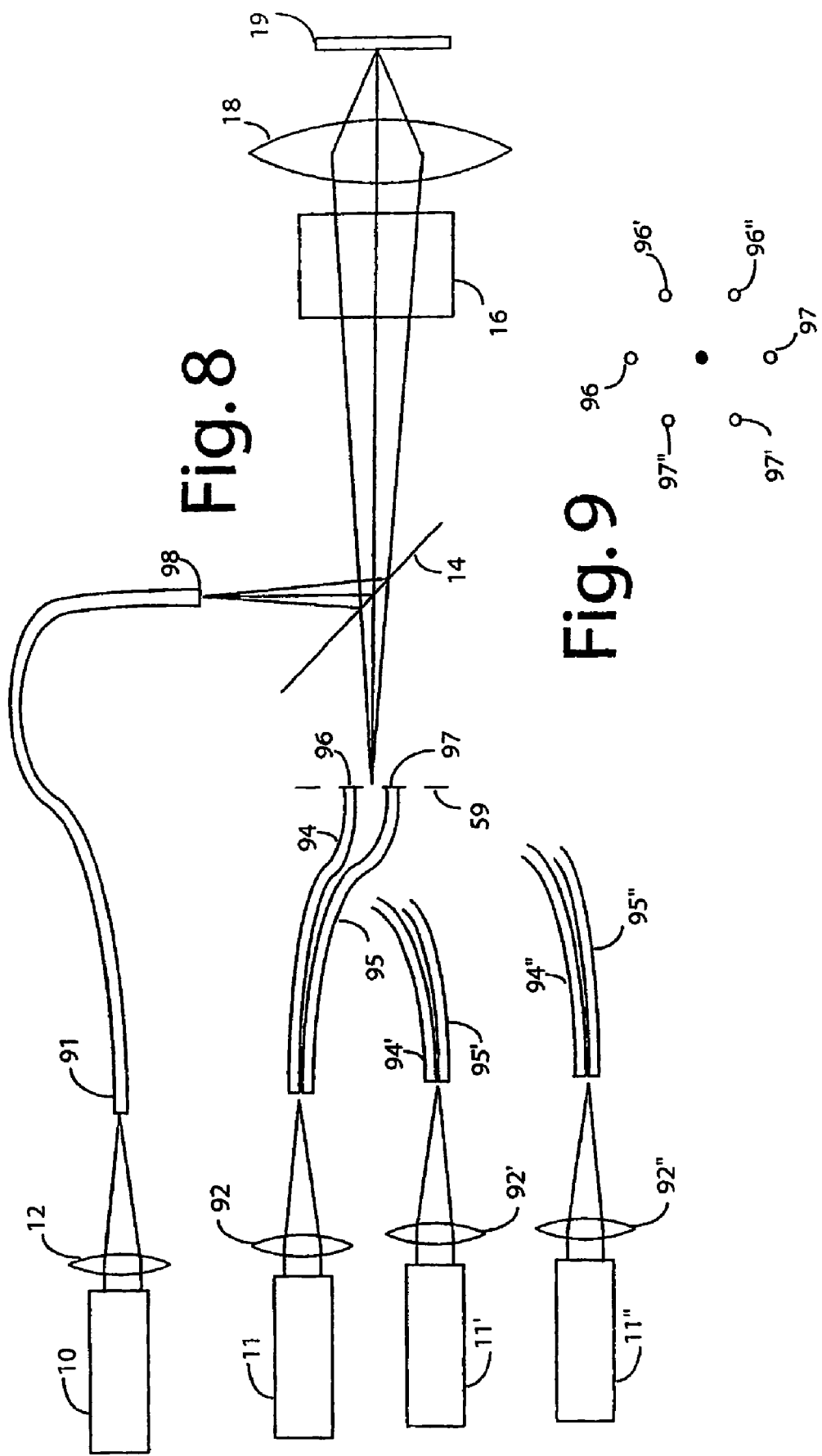

SUPERRESOLUTION IN MICROLITHOGRAPHY AND FLUORESCENCE MICROSCOPY

CROSS-REFERENCE TO RELATED APPLICATIONS

This application is a continuation of co-pending U.S. patent application Ser. No. 11/147,792 filed Jun. 7, 2005 now U.S. Pat. No. 7,071,477, which is hereby incorporated by reference, which is a continuation of U.S. patent application Ser. No. 09/902,902 filed Jul. 9, 2001, now U.S. Pat. No. 6,903,347 which is hereby incorporated by reference, which is a continuation-in-part of U.S. patent application Ser. No. 09/343,054 filed Jun. 28, 1999, now U.S. Pat. No. 6,259,104, which is hereby incorporated by reference, which is a continuation-in-part of U.S. patent application Ser. No. 08/919,382 filed Aug. 28, 1997, now U.S. Pat. No. 5,952,668, which is hereby incorporated by reference, which is a continuation-in-part of U.S. patent application Ser. No. 08/581,185 filed Dec. 29, 1995, now U.S. Pat. No. 5,777,342, which is hereby incorporated by reference, which is a continuation-in-part of U.S. patent application Ser. No. 08/275,967 filed Jul. 15, 1994, now U.S. Pat. No. 5,866,911 which is hereby incorporated by reference.

FIELD OF THE INVENTION

The present invention relates to scanned optical systems in which a beam of light is focused to the smallest possible spot in a specimen in order to selectively excite, within the illuminated spot, an excitable species such as a fluorescent dye, and more specifically to a method of improving the resolution of such system.

BACKGROUND OF THE INVENTION

In many fields of optics, a light beam is focused to the smallest possible spot in a specimen in order to selectively photoexcite a molecular species in the illuminated spot. Such fields include scanned beam fluorescence microscopy, scanned beam microlithography, nanofabrication, and optical digital information storage and retrieval. The lenses in such resolution demanding applications often approach diffraction limited performance, and in view of the dependence of resolution on wavelength and numerical aperture of the objective focusing the light, these lenses are designed with the largest practical numerical apertures and used with light of the shortest practical wavelengths.

Additionally, a variety of techniques have been devised to push resolution beyond the Abbe limit set by diffraction theory (S. Inoué, p. 85 in D. L. Taylor and Yu-li Wang, Fluorescence Microscopy of Living Cells in Culture, Part B, Academic Press, 1989). These techniques include placing annular and multiannular apertures in the aperture plane of the objective (Toraldo di Francia, Nuovo Cimento, Suppl. 9:426 (1952)) and using scanned confocal optics (M. Minsky, U.S. Pat. No. 3,013,467 (1961)). While in theory, such aperture plane apertures can allow arbitrarily narrow central mama of the point spread function, any substantial narrowing of the central maximum is accompanied by dramatically less efficient light utilization and degraded image contrast. Although, as originally pointed out by the inventor of the present invention (Baer, U.S. Pat. No. 3,705,755 (1972)), this problem of degraded contrast can be reduced by the use of such aperture plane apertures in a confocal scanning system, such a solution does nothing to improve the inefficient use of light actually reaching the specimen, so that in practice, light induced damage of the specimen or photobleaching of the fluorescent dye could limit the usefulness of such an approach. The technique of scanned probe, near field microscopy (Lewis et al U.S. Pat. No. 4,917,462) has had more success in achieving high resolution, but this technique is limited to the exposed surface of flat specimens. A related technique applicable only in the special case of optical disc recording and playback, involves the deposition, adjacent to the information containing layer, of an opaque layer which is be made to undergo a change an optical property such as transparency by a focused beam (Fukumoto and Kubota, Jpn. J. Appl. Phys. 31:529 (1992) Yanagisawa and Ohsawa, Jpn. J. Appl. Phys. 32:1971(1993), Spruit et al, U.S. Pat. No. 5,153,873 (1992)).

Though the variety of proposed superresolution techniques attests to the long recognized need to improve the resolution of the light microscope for applications such as the far-field imaging of typical specimens such as sections of biological tissue, it appears that the practical gains for such applications have been effectively limited to less than a doubling of resolving power relative to the Abbe limit. Thus any system which could increase resolution beyond the state of the art, and especially one which could work in conjunction with present superresolution techniques to further extend resolution performance, could be of great value in the field of light microscopy and other fields of scanned optics.

OBJECTS AND ADVANTAGES

It is the primary object of the present invention to improve resolution in optical systems such as scanned fluorescent microscopes, in which, at each moment, a beam of light is focused to the smallest possible spot in a specimen to excite an excitable species in the spot.

Another object of the present invention, in such systems, is to minimize the light induced damage to a specimen resulting from photodynamic action.

Another object of the present invention in such systems, is to minimize light induced bleaching and photolysis of the molecules responsible for absorption and emission.

Another object is to produce a method of fluorescent microscope resolution enhancement which is easily adapted to current laser confocal microscopes, two-photon excitation laser scanning microscopes, and fluorescent decay time contrast microscopes.

Another object is provide a method of resolution enhancement which will work synergistically with known superresolution methods thereby increasing the resolution over these known techniques.

Another object is to allow high resolution epiillumination imaging of living biological specimens at greater tissue depths from the surface than is possible with current techniques.

Another object is to provide a resolution enhancement technology which can be adapted to the fields of high resolution photolithography, nanofabrication and digital computer memory storage and retrieval.

Another object of the invention is to avoid image degradation due to coherence effects of laser illumination, while using such coherence instead to increase resolution.

Still other advantages of the present invention will become evident in this disclosure.

SUMMARY OF THE INVENTION

The foregoing objects are achieved and the foregoing problems are solved in one illustrative embodiment of the invention, applied specifically to the field of fluorescence microscopy, although the principles embodied therein also apply to the other applications of the present invention discussed in this specification. This embodiment is an improvement of the laser scaring fluorescence microscope, wherein a scanned excitation beam is focused to a diffraction limited spot size and illuminates successive spots in a fluorescent specimen, exciting fluorescent dye molecules within these spots to fluorescence. Fluorescent light emanating from each of these illuminated spots is then electronically measured, and a spot of light the intensity of which varies in accordance with the measured fluorescence from these illuminated spots is scanned over a video monitor screen in correspondence with the scanning of the excitation beam over the specimen, to create a final image of the specimen. In the present invention, light of a wavelength adapted to quench fluorescent excitation of the excited dye molecules is focused in the specimen to a pattern containing a central minimum which is made concentric with the central maximum of the exciting radiation, the central points of the central maximum of the exciting beam and of the central minimum of the quenching beam substantially coinciding, so that within the central minimum region, the intensity of the quenching beam, and consequently the degree of quenching of the fluorescence, increases with distance from the central point, thereby decreasing the effective width of the distribution of probability of fluorescent excitation as a function of distance from the center of the illuminated spot, and consequently increasing the effective resolving power of the microscope. In the preferred embodiment of the present invention, the central minimum is narrowed by creating the pattern of quenching radiation in the specimen by imaging onto the focal plane a plurality of pairs of sources of quenching light, arrayed in a regular, even-sided polygon, such that the two members of each pair are on opposite vertices of the polygon and emit light mutually coherent and out-of-phase, and the light emitted by different pairs is incoherent with respect to each other.

BRIEF DESCRIPTION OF THE DRAWINGS

The principles of the invention will be more particularly discussed with reference to the accompanying drawings in which:

FIG. 8 is a schematic cross-sectional view of the present invention wherein the resolution of the device is improved by forming the quenching beam by imaging onto the specimen the ends of a set of laser-illuminated optical fibers arrayed at the vertices of an even sided polygon, such that the laser output of diagonally opposite fibers is out-of-phase, and the laser output of adjacent fibers is mutually incoherent;

FIG. 9 is a view showing the arrangement of the non-illuminated ends of the fibers in the device shown in FIG. 8;

DESCRIPTION OF THE INVENTION

Figure 1:
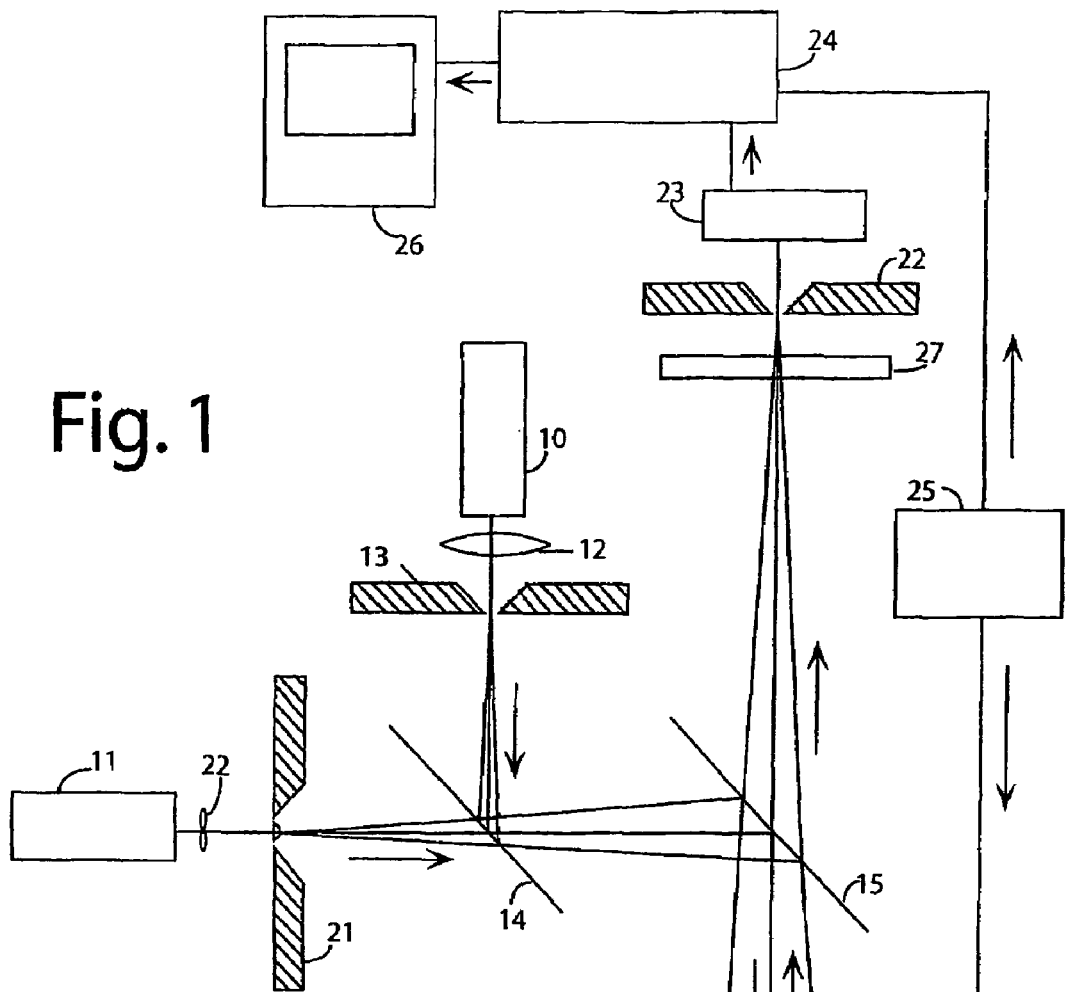
FIG. 1 is a schematic cross-sectional view of a scanning fluorescence microscope embodying the invention.
Figure 2:
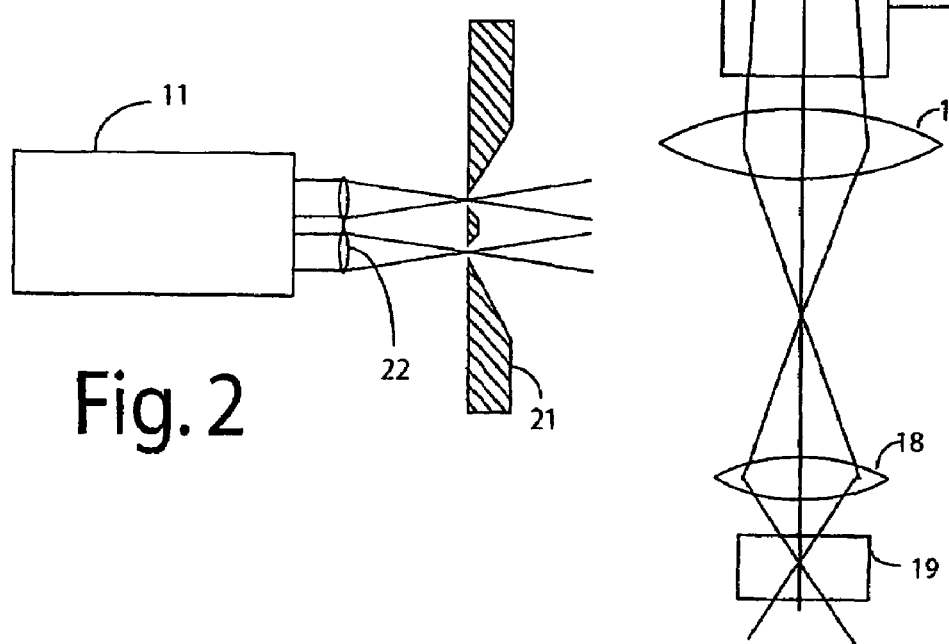
FIG. 2 is an enlarged detail showing a portion of the device shown in FIG. 1.

FIG. 1 shows an embodiment of the present invention employing continuous wave laser illumination. Light from excitation laser 10 is focused by lens 12 onto pinhole aperture 13, and after passing through aperture 13, reflection from dichroic mirror beam splitters 14 and 15 and scanning by beam scanning means 16 (which may be a pair of orthogonal galvanometer powered scanning mirrors) the laser light is imaged by eyepiece 17 and objective 18 on or within the specimen 19 stained with fluorescent molecules excitable by light emitted by laser 10, to form a region of excited fluorescent molecules at the image of pinhole aperture 13. Quenching laser 11, which emits light of a wavelength adapted to quench, by means of stimulated emission, the fluorescent excitation caused by laser 10, is focused by toroidal lens 22 onto annular aperture 21. Light passing through aperture 21 passes through dichroic beam splitter 14, then is reflected by dichroic beam splitter 15 to pass through the beam scanning means 16, and is focused by eyepiece 17 and objective 18 onto specimen 19. In FIG. 1, for purposes of illustration only, rays are show emanating from the central point of annular aperture 21 to simplify the illustration and to show that this central point is conjugate, with respect to beam splitter 14, to the central point of pinhole aperture 13, and it should be understood that since this central region of annular aperture 21 is in fact opaque, rays do not actually emanate from this central point. In FIG. 2, a magnified detail showing laser 11, toroidal lens 22 and annular aperture 21, the rays are correctly shown focused by lens 22 onto and then emanating from the transparent ring of aperture 21. The mirror image relationship between the center of annular aperture 21 and pinhole aperture 13 insures that the projected image in the specimen 19 of annular aperture 21 is concentric with the image in the specimen of pinhole aperture 13. The diameter of annular aperture 21 is chosen so that the diameter in the specimen of the central ring of maximum intensity is the same as the diameter of the first minimum of an Airy disc point diffraction image which would be formed at the wavelength of the quenching laser 11. This means that the diameter in the specimen of the ring of maximum intensity for the quenching radiation is larger than the diameter of the first minimum of the point diffraction image of pinhole 13 by the ratio of the wavelength of the quenching laser to the wavelength of the excitation laser.

Objective 18 collects fluorescent emission from those excited fluorescent molecules in the specimen, in the focus of the excitation beam, which have not been quenched by the quenching beam. This emission, after passing through objective 18 is directed successively through eyepiece 17, beam scanning means 16, beam splitter 15, and blocking filter 27 adapted to block reflected excitation and quenching light, to viewing pinhole aperture 22, which is conjugate to pinhole aperture 13. Emitted light passing through aperture 22 is detected by photodetector 23 (which may be a photomultiplier tube) the output of which is directed to video frame store 24, which is synchronized by the scan drive circuit 25 which powers the beam scanning means 16. The information contents of the video frame store 24, as manipulated by appropriate image processing means, is displayed on video monitor 26, producing an image of the scanned plane of the specimen 19.

Figure 3:
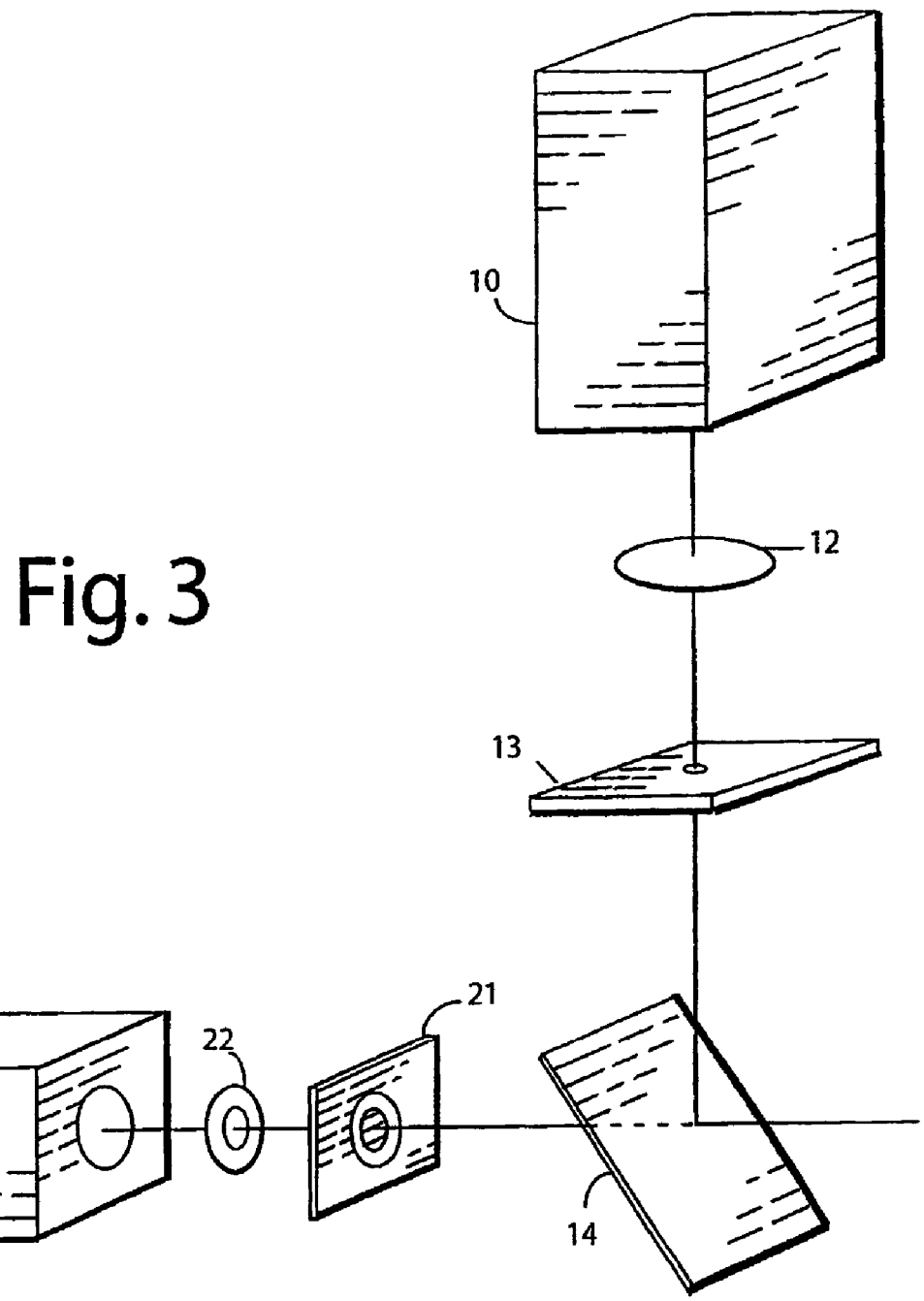
FIG. 3 is a perspective view showing a portion of the device of FIG. 1.

FIG. 3 shows a perspective detail of a portion of the apparatus of FIG. 1. It should be noted that for purposes of illustration, the openings of pinhole aperture 13 and annular aperture 21 are shown larger than the scale of the rest of the elements in this figure. Although in principle, completely different optical systems could be used to project a central minimum of quenching radiation so its center coincides in the spin with the central point of the central maximum of the exciting radiation, for use in a scanning microscope application, the sharing of focusing optics, made possible by the use of beam splitter 14, insures that provided the focusing and scanning systems are achromatic, the required coincidence between the central points of these images will be guaranteed even at the precision required in high resolution microscopy, once the apertures 13 and 21 are aligned at one scan position, because perturbations, for example due to inhomogeneities in the specimen above the plane of focus, distort the excitation and quenching beams equally. In case focusing optics which have been achromatized for the choice of excitation and quenching wavelengths are unavailable, it is possible to longitudinally shift aperture 21 relative to the position conjugate to aperture 13 with respect to beam splitter 14, so that the images of the two apertures are coplanar and concentric in the specimen. Since such an arrangement will only provide correction for the axial focal point, scanning can be provided in such an arrangement, for example by lateral movement of the specimen.

Figure 4:
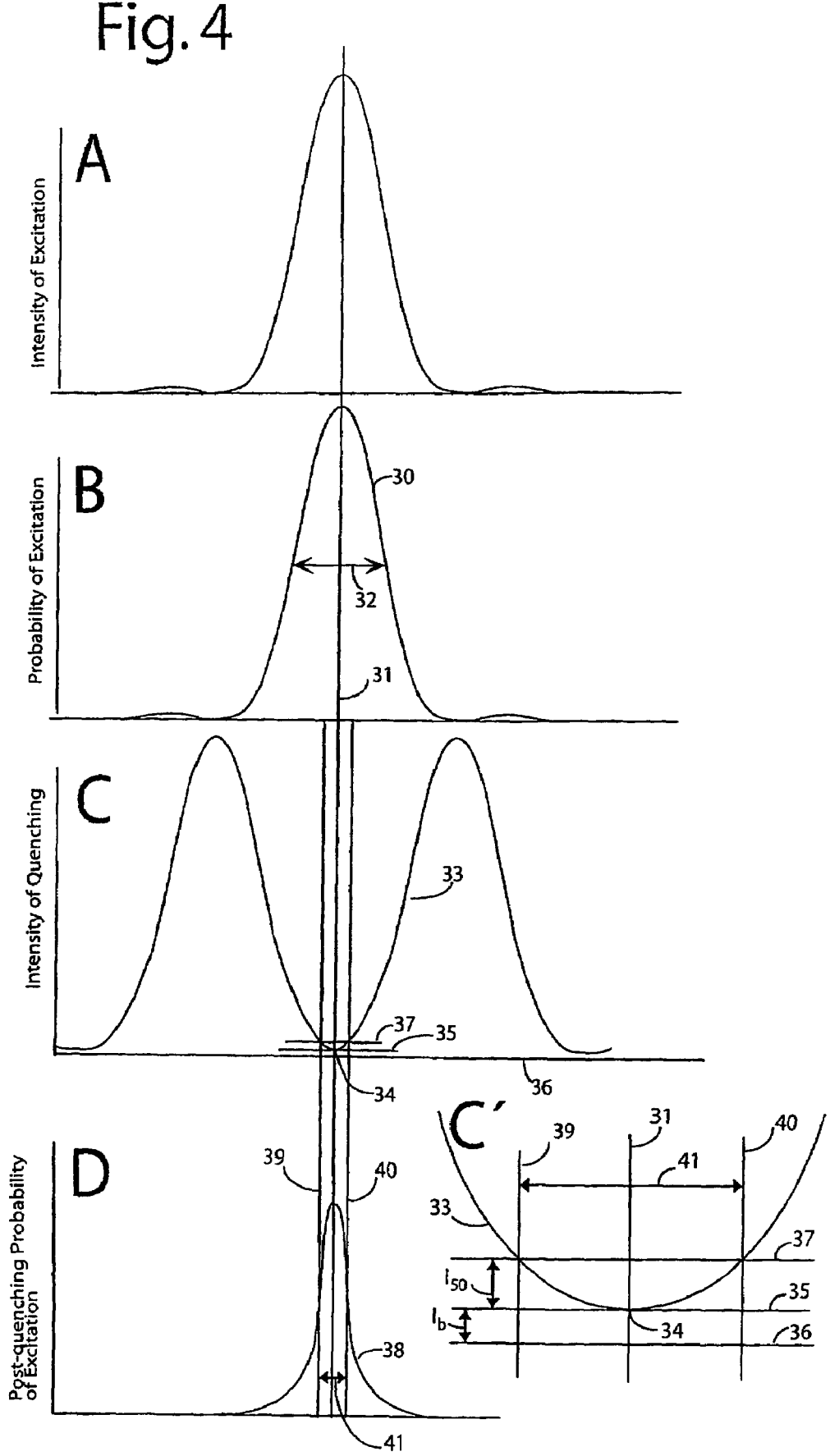
FIG. 4 is a graph showing the intensity distributions at the plane of focus for the excitation and quenching beams, and the resultant fluorescence excitation probability distribution due to the joint interaction of these beams with the specimen.

Why the present invention will cause an improvement in resolving power is shown in FIG. 4, which shows how quenching, applied according the present invention, can reduce the nominal width of the distribution indicating the probability that a given probe fluorescent molecule in the specimen will be in its excited state, as a function of the distance of this molecule from the center of the central maximum of the focused excitation beam. To simplify this illustration, it is assumed that this probability of excitation of the fluorescent molecule is proportional to the intensity of exciting illumination incident on the molecule. Secondly, the illustration is applied specifically to the imaging of the central spot of the imaging field, where the center of the spot intersects the optical axis of the objective 18.

FIG. 4A shows the expected light intensity distribution of the "Airy disc" or diffraction image of excitation pinhole aperture 13 projected in the specimen 19 by objective 18. The use of the axial point as the example in this illustration means that the spatial coordinate in the distribution is simply the distance, in the plane of focus, from the axis of objective 17, this distance being shown by distance from the vertical line 31 common to FIGS. 4A, B, C and D. The vertical axis in these figures represents either light intensity or excitation probability, where the upward direction corresponds to increases. The description of imaging of non-axial points is somewhat more complicated than this present axial case, but resolution enhancement works in the same way. FIG. 4B shows the probability of excitation 30 of a fluorescent molecule as a function of the distance in the focal plane between the axis and that molecule. The assumption of a proportional excitation response by the fluorescent molecule means that this excitation probability distribution 30 shown in FIG. 4B is proportional to the diffraction image distribution shown in FIG. 4. In a case where the excitation probability was not proportional to excitation intensity, for example because excitation saturated the population of fluorescent molecules causing the top of the central maximum of curve 30 in FIG. 4B to be flattened with respect to the curve of FIG. 4A, the following arguments for the shrinkage of the width of the excitation probability curve are still valid.

The nominal width of the central maximum of the excitation probability distribution (without any resolution improvement due to quenching) is shown by the double arrow 32, which measures the distance between the two points in the distribution where the probability of excitation is half maximal. (When this distribution is imagined in the two dimensions of the plane of focus, double arrow 32 indicates the diameter of the circle where the probability of excitation is half the maximum probability). The object of the present invention is to apply the quenching radiation in a pattern which preferentially decreases the probability of resulting excitation in peripheral portions of the central maximum of the excitation probability curve, while sparing, as much as possible, the probability of excitation in the central portion, thereby narrowing the nominal width of the probability of excitation curve.

FIG. 4C shows the expected intensity distribution 33 of the image, projected in the specimen, of annular aperture 21, which is illuminated by the quenching beam. The mean radius of annular aperture 21 is such that, by diffraction theory, the diffraction image in the specimen resulting from the contribution from of each small section on the ring of annular aperture 21, taken in isolation, has an intensity of zero on the optical axis (i.e., the first minimum passes through the optical axis), so that as the light emanating from each of the small sections on the ring of aperture 21 summates to create an image of annular aperture 21 in the specimen, the sum, at this central axial point, of the zero intensities from each of the sections of the aperture 21 still adds to zero. However, scattering in the optics of the instrument and in the specimen, and reflections from lower lying layers of the specimen, causes the central minimum on the optical axis, in fact, to have a small but finite intensity $I_b$ shown by the horizontal line 35, which is above the zero intensity baseline 36. The term "central minimum" is used herein analogously to the more common expression "central maximum" and refers to the fact the image has a minimum at its center, even if the image as a whole is not centered with respect to the optical axis, as when non-axial points are imaged.

In the following discussion it is assumed that once a given fluorescent molecule is excited, it has a probability p of eventually emitting a fluorescent photon, and that for a wide range of initial conditions, such as different mixtures of exciting vs. quenching light, and different concentrations of fluorescent molecules, that adding to the existing light mixture the same intensity of quenching light, called $I_{50}$, which is different for different species of fluorescent molecule, will reduce p to half its value before such addition. It should be emphasized that the assumption may not be completely valid in view of factors such as saturation, but it will nevertheless help illustrate several aspects of how quenching can improve resolution.

For a given total power of the quenching beam and a given species of fluorescent molecule, it is possible to see approximately how much sharpening of resolution will result with the present system by determining the intensity of quenching radiation which must be mixed with an excitation beam to reduce its effective rate of excitation of the fluorescent molecules by 50%. This intensity is shown by the double arrow labeled $I_{50}$ in FIG. 4C, which shows a detail from FIG. 4C in magnification.

It is assumed that due to factors such as scattering in the optics and the specimen, there is a small but finite intensity of the quenching beam at the central point of the central minimum of the quenching beam, shown by the double arrow labeled $I_b$. The addition of more quenching light of intensity $I_{50}$ therefore will bring the total intensity of quenching light to the level shown by the line 37 which has a intensity of $I_b+I_{50}$. By definition of $I_{50}$, then, at the distance from the central maximum where the intensity of the quenching beam is $I_b+I_{50}$, shown by the vertical lines 39 and 40, the efficiency of excitation in producing a latent image is half the efficiency in the center of the central maximum. Because the excitation beam is also most intense at the center, the full width at half maximum of the probability-of-fluorescent-emission curve, post quenching, is actually narrower than the distance between lines 39 and 40, shown by the double arrow 41. It can be seen that by simply increasing the total power of the quenching beam, that the double arrow 41 can be arbitrarily reduced. FIG. 4D shows the distribution 38 of the probability of fluorescent molecule excitation, subject to quenching by the quenching beam (the effective excitation, correlated with the probability of ultimate fluorescence emission), and it can be understood that this distribution can be arbitrarily narrowed, by reducing double arrow 41 by means of increasing the quenching beam power.

Of course, there is a limit to how much quenching radiation can be directed onto the specimen before it is damaged by heating therefore the ability of the specimen to tolerate high quenching beam powers may be the major resolution determining factor in the present system for microscopy or microchip fabrication. Furthermore, it will be appreciated that as the total power for the quenching beam increases, so does the intensity of the central point of the central minimum, $I_b$, and consequently the effective sensitivity of the process is reduce. Therefore another design objective in the present system is to reduce the intensity of the central point of the central minimum of the quenching beam to the lowest practical level, in order to preserve the sensitivity of the process, while achieving good resolution improvement.

FIG. 4 also shows that only a small part of the energy of the quenching beam, in the central part where the intensity is lowest, is involved in resolution enhancement. This means that for each milliwatt of laser energy needed in the crucial central part of the quenching laser beam, a total beam power of perhaps hundreds of milliwatts may be required. However such powers are easily attainable with available lasers. Furthermore, high intensities of the quenching beam in the bright ring surrounding the central minimum do not degrade the image because the final excitation probability of the fluorescent molecule can never be lower than zero, so high quenching intensities will saturate at zero net excitation. Therefore, from the point of view of image quality, the intensity of the quenching beam can be adjusted for optimal sharpening at the center of the intensity minimum, without worry about the high intensities surrounding the central minimum. By choice of a quenching wavelength where there is negligible absorption by the specimen except by excited fluorescent molecules, thermal effects on the specimen of the quenching beam are minimized. Thermal effects might also be reduced by use of diamond or other high thermal conductivity material as a support for the specimen.

Another possible concern about the high intensity of quenching radiation is that some stray radiation could enter the photodetector, degrading image contrast. However both filter 27 and dichroic mirror 15 block such quenching radiation from entering the detector. Additionally, in forms of the invention using pulsed radiation, quenching light can be eliminated by gating off the detector sensitivity during times the quenching light is on. From the point of view of specimen and fluorophore damage, in the presence of excited fluorophores capable of producing photodynamic damage, quenching radiation can reduce such damage by deexciting the excited species. Therefore, by choice of a quenching wavelength where there is negligible absorption by the specimen except by excited fluorophore molecules, high quenching intensities are not simply tolerable, but can actually be beneficial.

Under the same conditions described above to produce the minimum in the focal plane, which is perpendicular to the optical axis, the intensity distribution measured along the optical axis also has a minimum sharing the same central point. With microscope objectives generally, the width of the central maximum of the point diffraction image, measured in the focal plane perpendicular to the optical axis, is smaller than the width measured along the optical axis resulting in a better lateral resolution than longitudinal resolution. This same elongation along the optical axis occurs with the central minimum of the diffraction image of the annular aperture 21, so that in general, following resolution enhancement by the apparatus shown in FIG. 1, longitudinal resolution will also be improved by quench sharpening, but the lateral resolution will still be better than the longitudinal resolution.

Because (at least near the focal point) excitation of the fluorescent molecule due to the cone of rays converging to the focal point and the cone of rays diverging from the focal point is eliminated by quenching, only the in-focus rays at the focal point remain for production of the fluorescent image. Therefore the present system (in common with confocal microscopes) permits extending the practical depth-of-focus, by scanning in depth in addition to scanning laterally. This is particularly useful in more parallel forms of image formation discussed below, where the same image would be formed at many different closely spaced focus settings, to produce a composite image which is sharp at every depth of the specimen. Additionally, by increasing the intensity of the image for deeper layers, it is possible to compensate for absorption of the excitation light by superficial layers of the specimen.

Figure 5:
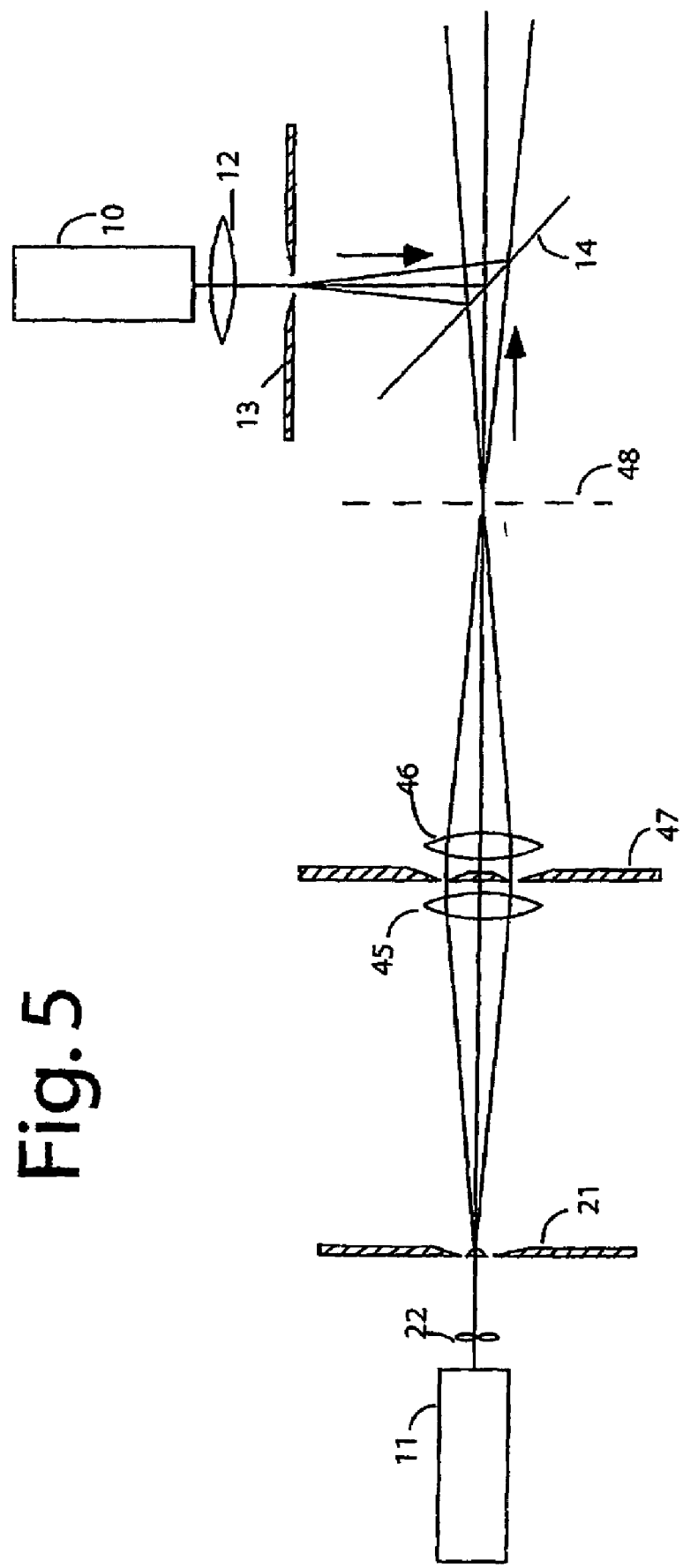
FIG. 5 is a schematic cross-sectional view of a portion of a variant of the device shown in FIG. 1 to illustrate the use of an annular aperture in an aperture plane to further increase resolving power.

FIG. 5 shows how the resolution of the present invention might be increased by combining the field plane annular aperture used in the present invention to create in the specimen a quenching beam pattern with a central minimum with an aperture plane annular aperture to improve the lateral resolution of that quenching beam pattern. (Born and White, Principles of Optics, 3rd edition, p. 416). A relay lens system consisting of lenses 45 and 46 with annular aperture 47 in an aperture plane, images annular aperture 21 onto a real image plane 48 which is corrugate to pinhole 13 relative to the beam splitting mirror 14 (i.e., real image plane 48 is in the same plane as annular aperture 21 in FIG. 1 before being displaced to the position shown in FIG. 5). The diameter of annular aperture 21 is readjusted to cause the central minimum in its image in the specimen have a minimum intensity. The use of an aperture plane annular aperture 47 in addition to the field plane annular aperture 21, causes the central minimum in the specimen to have a smaller width, to improve lateral resolution, and at the same time to have a reduced resolution in the axial dimension for improved depth-of-field. Instead of the annular aperture 47 in the aperture plane of the relay lens system, there can be a complex aperture of different annuli, each with specified phase retardation and opacity, for further decreases in the width of the central maximum, as shown originally by Toraldo di Francia (Nuovo Cimento, Suppl. 9:426 (1952)). It should be noted that in the design of such an aperture plane aperture 47, it is more important to maximize the sharpness of the first minimum of the point spread function rather than the usual design criterion of maximizing the sharpness of the central maximum. (The central minimum might also be "sculpted" to optimize, for example, a particular desired tradeoff between image brightness and resolution, by replacing the uniform ring of aperture 21 with a series of annuli of independently controllable phase retardation and absorption, in addition to the choice of phase retardations and absorptions for annular rings in the aperture plane aperture 47.) It should also be appreciated that a major problem with Toraldo type aperture plane apertures, namely the defection of beam power away from the central maximum, causing problems of reduced contrast and increased photobleaching and photodynamic specimen damage, are overcome in the present invention, because, as described above, light from the quenching beam outside the central minimum, does not degrade image contrast or increase photobleaching or photodynamic damage.

Figure 6:
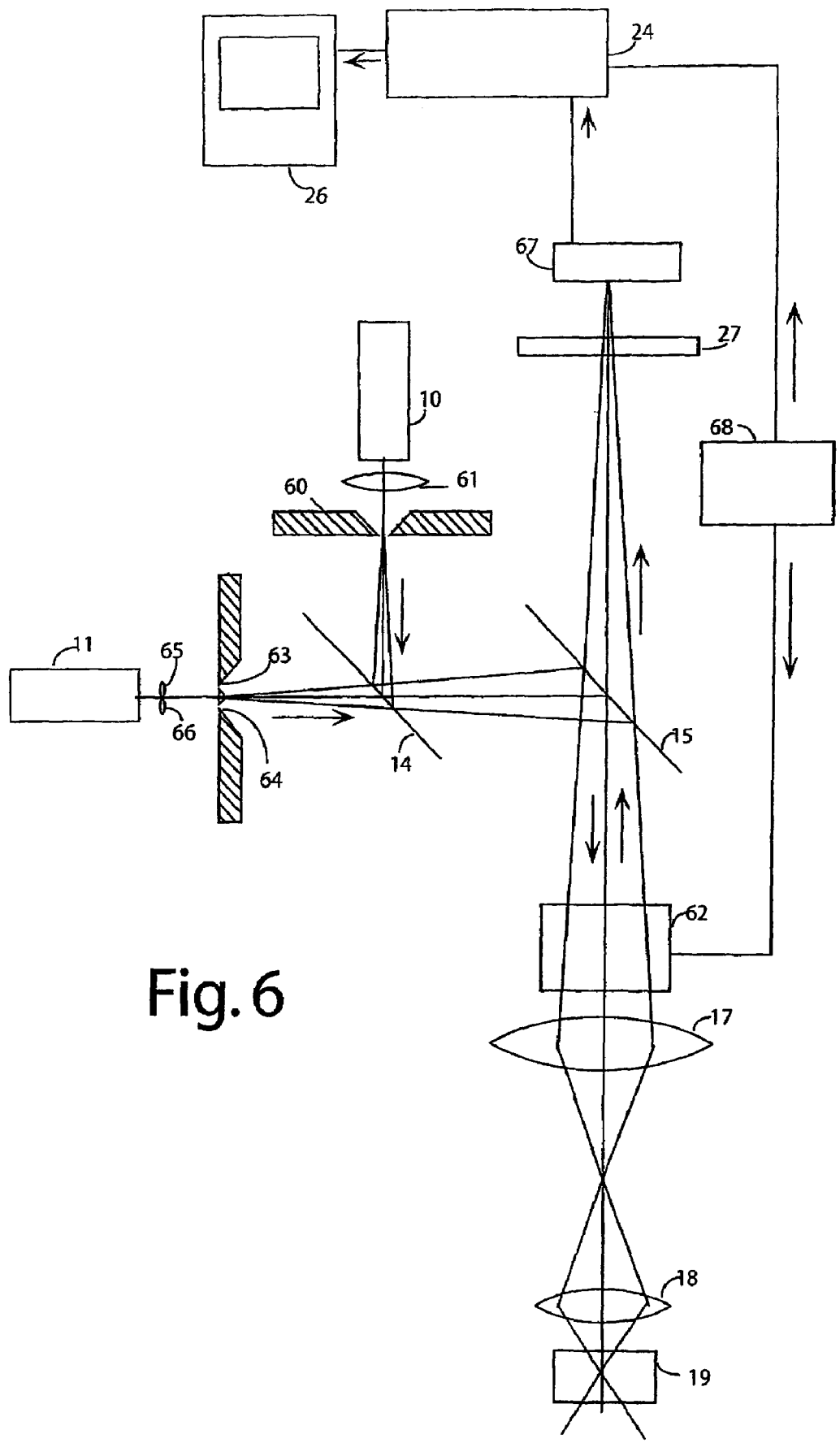
FIG. 6 is a schematic cross-sectional view of an embodiment of the present invention using slit apertures.

FIG. 6 shows an embodiment of the present invention where the pinhole aperture 13 of FIG. 1 is replaced by a slit aperture 60, which is illuminated by the same excitation laser 10 as in FIG. 1, but where the beam emanating therefrom is focused by cylindrical lens 61 to a line coincident with the slit in aperture 60. Slit aperture 60 in the cross sectional view of FIG. 6 appears identical to the cross-sectional view of pinhole aperture 13 in FIG. 1. The beam emanating from aperture 60 is reflected successively by dichroic mirror beam splitters 14 and 15, identical to those shown in the device of FIG. 1, and is passed through beam scanning means 62, which differs from the scanning means 16 of FIG. 1 because it is required to scan in just one dimension. The scanned beam is focused successively by the eyepiece 17 and objective 18 lenses onto specimen 19, identical to those of FIG. 1, however the image of the excitation beam in the specimen 19 is an illuminated strip, with a central maximum which is elongate in the dimension parallel to the strip. The nominal width of such an elongate central maximum is defined herein as the distance between the lines where the intensity is half-maximal. The quenching laser 11 is directed on two parallel slits 63 and 64, by means of two parallel cylindrical lenses 65 and 66. The spacing between slits 63 and 64 is such that the first minima of their diffraction images in the specimen 19 coincide to produce a central minimum, made to coincide with the central maximum of the diffraction image in the specimen of slit 60, such that the central line of the central maximum coincides with the central line of the central minimum of the used quenching light. Fluorescent emission from specimen 19 is focused by successive objective 18 and eyepiece 17 lenses to focus light from the central maximum in the specimen onto a linear photodiode array 67, oriented perpendicular to the plane of FIG. 6. The output from array 67 is stored in video frame store 24 which is synchronized by the output of the scan drive circuit 68 which drives the one dimensional beam scanner 62.

The advantage of a one-dimensionally scanned strip arrangement as in FIG. 6 compared with a two dimensionally scanned spot arrangement as in FIG. 1, is that one less dimension in scanning is required, so much faster scans at a higher scan frequency can be produced, and the apparatus is simpler. The disadvantage is that the resolution gain of the present invention is secured only in one dimension. However for many applications a gain in resolution in just one dimension is sufficient, and the simplicity and scanning speed of the slit arrangement are preferred. It should be noted that instead scanning produced by beam scanning means 16 or 62, the required relative movement between specimen and the image of the focused light beams in the specimen can be produced by movement of the specimen, or an optical element in the light path between the light source and the specimen, synchronized with the image acquisition process of frame store 24.

Figure 7:
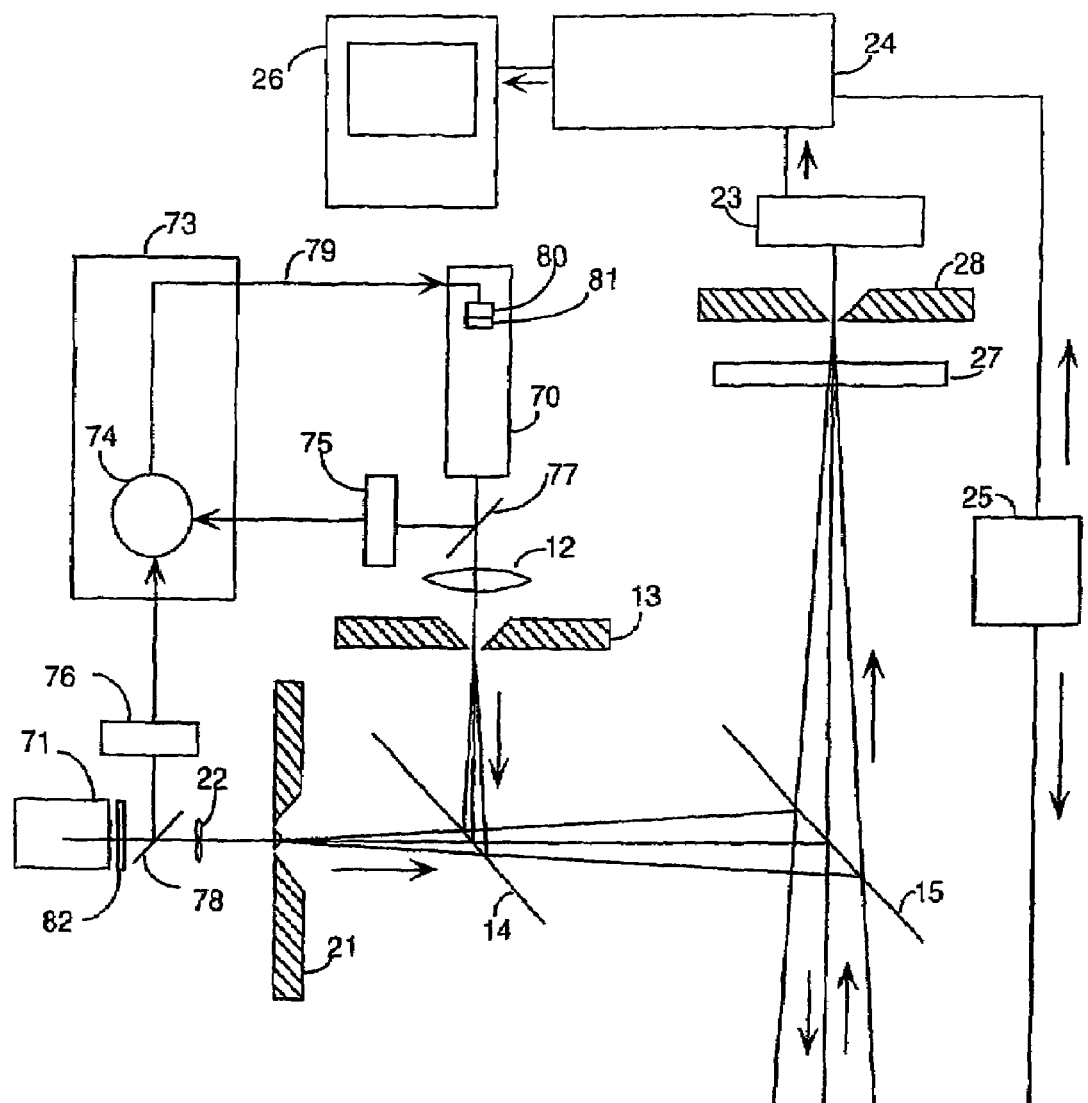
FIG. 7 is a schematic cross-sectional view of the present invention wherein the excitation and quenching beams are presented as successive ultrashort pulses.

FIG. 7 illustrates an embodiment of the present invention employing synchronized ultrashort-pulse (shorter than a few picoseconds), repetitively pulsing lasers for excitation and quenching. In particular, the pulse output from the lasers is adjusted so that the quenching beam is turned on within picoseconds of the offset of the excitation beam before there has been any time for significant fluorescent emission, so that virtually all such emission will follow the offset of the quenching beam. There are significant advantages of such a pulsed laser embodiment of the present invention compared to embodiments wherein the excitation and quenching beams are continuously on. Most importantly, there is more efficient quenching per watt of average quenching beam power. This may be understood from a specific example where the excitation pulse frequency is assumed to be 100 MHz, and the fluorophore is assumed to have a 1 ns half-life for the excited state. (For the purpose of this example it is assumed that the fluorophore is very efficient, so in the absence of optical quenching, the excited state decays almost exclusively by fluorescent emission.) If it is assumed that each quenching photon incident on the fluorophore has a 20% probability of quenching it, then 10 incident photons together would have about a 90% chance of producing quenching. If these 10 quenching photons were delivered within several picoseconds following each excitation, then substantially all the quenching would take place before there was an opportunity for fluorescence so the resulting quenching would be 90%. However if these 10 quenching photons were emitted by a continuous wave laser, so they arrived spaced over the 10 ns interval between excitation pulses, after the first nanosecond, there would have been roughly a 50% likelihood of fluorescent emission, but only roughly a 20% likelihood of quenching, and obviously any quenching photons which arrive after the fluorescent emission have zero effect. In other words, bunching the photons in the interval immediately after excitation greatly improves the quenching efficiency. The quenching efficiency can be further increased in a pulsed system by making the excitation and quenching lasers have the same polarization, so there is insufficient time for a significant change in direction of polarization by rotation of the fluorophore between excitation and quenching, hence the quenching laser will be optimally aligned with the excited molecules.

The pulsed laser embodiment of the present invention shown in FIG. 7 has additional advantages. The ultrafast laser excitation makes it convenient to excite fluorescence by two-photon absorption (Denk, et al Science 248:73 (1990), Denk, et al U.S. Pat. No. 5,034,613 (1991)), which substantially confines light induced damage and photobleaching to the plane of focus, and provides illumination with light of a relatively long wavelength which can penetrate to greater depths of tissue. Unfortunately, with state of the art two-photon microscopy, the advantage of limitation of excitation to the plane of focus is gained (for a given fluorophore) only with some loss of lateral resolution (Sheppard and Gu, Optik 86:104 (1990)). However in the present invention, the quenching beam rather than the excitation beam is the principal determiner of lateral resolution, so that two-photon excitation can be used for excitation, with the resulting confinement in excitation, and the use of single-photon absorption for quenching insures high lateral resolution. Still an additional advantage of the pulsed embodiment shown in FIG. 7 is that it allows laser dyes and their local environments to be characterized by fluorescence lifetime measurements, with minimum additional equipment costs. Furthermore, with a photodetector 23 that is not blinded by direct reflections from the laser pulses, time discrimination can replace the wavelength discriminating blocking filter 27, thus avoiding one source of potential light wastage.

In FIG. 7, excitation laser 70 and quenching laser 71 are ultrashort pulse mode-locked lasers, using, for example, optically pumped Ti-sapphire, dye or Cr-forsterite as the active medium. These types of lasers result in a repetitive train of pulses of durations from about 100 femtoseconds to several picoseconds, and at a frequency of about 50 to 100 MHz which depends on the length of the laser cavity. Lasers 70 and 71 are synchronized by means of a phased locked loop synchronizing circuit 73, which, by means of phase detector 74 detects phase difference between the amplified and filtered electrical outputs of high frequency response photodetectors 75 and 76, which receive a portion of the output beams of lasers 70 and 71 respectively by means of beam splitters 77 and 78. The output 79 of circuit 73, representing a correction signal to stabilize the desired phase difference between the pulse trains from the two lasers, is applied to a piezoelectric actuator 80 which controls the longitudinal position of one of the end mirrors 81 of the cavity of laser 70, thereby adjusting the laser pulse frequency, and thus stabilizing this phase difference. The desired phase difference, where the pulse from laser 71 follows the offset of the pulse from laser 70 by an interval from zero to several picoseconds can be adjusted either electrically in circuit 74, for example by adding a controlled phase shift to one of the inputs of phase detector 74, or optically by means of adjusting the optical path difference between the outputs of the two lasers. A commercially available unit to implement circuit 73 is the Model 3930 Lok-to-Clock™ Electronics Control from Spectra-Physics Lasers, Inc., Mountain View, Calif., which can be used when the lasers 70 and 71 are Spectra-Physics Model 3960C Tsunami™ Ti-sapphire lasers. FIG. 7 also shows a frequency doubling crystal 82, which can be optionally placed in the beam path of the quenching laser to halve the output wavelength. This doubling crystal 82 is representative of such frequency multiplying means which can be placed in the path of either laser to change the output wavelength. Both lasers 70 and 71 may be pumped by a common argon ion laser (unillustrated) with a divided output. Apart from the lasers 70 and 71 and their synchronizing apparatus, all the elements in the embodiment shown in FIG. 7 are substantially identical to and serve substantially the identical function to the respective elements shown in FIG. 1, so they are numbered with the same numerals as FIG. 1, and are described by the text corresponding to FIG. 1.

Many alternative methods of producing two beams of synchronized ultrashort pulses are known in the art. The synchronization between lasers 70 and 71 could be by means of a purely optical coupling, for example by having both lasers optically pumped by the pulsed output of a synchronous pumping laser (Moritz, N. et al, optics Comm. 103:461(1993)). Still another possibility is for a portion of the light output of the excitation laser 70 to be used as a synchronous pump energy source for the quenching laser 71 (or vice versa). Another possibility is to provide a single laser which emits ultrashort pulses in the near i.r., for example the 1.3 µm output of a Cr-forsterite laser in a self-modelock configuration, or the 1.5 µm, 2 ps, 27 MHz output of a Er, Yb doped fiber laser (Laser Focus World, July 1993 p. 15) and split the output into a portion directed through a frequency doubler crystal and a frequency tripler crystal to derive the quenching and excitation beams respectively. Furthermore, the recently commercially available optical parametric oscillator coherent light sources intrinsically produce simultaneous outputs at several wavelengths, which, if necessary, can be frequency multiplied to the range required for a broad range of fluorescent dyes. Finally it has been possible to produce two color pulses from the same laser (de Barros M. R. X. and Pecker, P. C., Optics Lett. 18:631(1993)), and the outputs could be separated by wavelength for use as the excitation and quenching beams.

The quenching radiation emitted by laser 11 or 71 must be of a wavelength adapted to induce stimulated emission from the fluorescent dye molecules in specimen 19, and consequently must be of a wavelength where there is significant fluorescent emission. Furthermore, it is important that this quenching radiation not itself fluorescently excite ground state fluorescent molecules. These simultaneous requirements may be met in several ways. In dyes such as the coumerin derivatives with relatively large Stokes shifts, the excitation spectrum has dropped to a negligible level in the long wavelength portion of the fluorescent emission spectrum. Alternatively, in a fluorescent dye with a large probability for transition between the ground vibrational level of the first electronically excited singlet (i. e., the fluorescently excited state) to the second vibrational level of the ground state, such that at the wavelength corresponding to this transition, there is still a significant emission likelihood, and hence a significant stimulated emission cross-section, but the wavelength is long enough that the absorption of the quenching light by the ground state fluorophores has dropped to essentially zero. When used for biological microscopy, additional desired attributes for a dye in the present application which are also generally desirable for any fluorescent dye in a biological microscopy application are that it have a high fluorescent efficiency, that it be commercially available in forms such as antibody and dextran conjugates, and that it have a low intersystem crossing probability for production of triplet states (or be self quenching for triplet excitation). A large two-photon excitation cross-section leaves open the possibility of excitation by two-photon excitation. Finally, the excitation and quenching wavelengths must be chosen with respect to cost and availability limitations of the excitation and quenching lasers.

The choice of wavelength of excitation and quenching is also subject to a tradeoff since shorter wavelengths lead to increased resolution by the classical resolution criteria, whereas longer wavelengths, especially above 630 nm (Puppels, G. J., et al, Exptl. Cell. Res. 195:361(1991)) are reported to be less toxic to biological tissue at high power densities and can penetrate biological tissue with less scattering. In fact, as discussed, the lowering of scattering may be more critical to achieving good resolution in the present invention than the resolution performance as predicted by diffraction theory for a non-scattering medium, because it may allow a lower intensity at the central minimum of the quenching beam focus. In case it is necessary to use a quenching beam in a part of the spectrum which can be injurious to the specimen, these quenching photons can be used most efficiently by insuring that the just preceding excitation pulse was of sufficient intensity to nearly saturate the fluorescent excitation. For relatively inefficient fluorescent dyes this may require reducing the frequency of the pulse output of laser 70, so that for a given time averaged power output, the power per pulse increases. On the other hand, with an efficient fluorophore, there might be near saturation with each pulse, even with a few milliwatts average beam power and a frequency of about 80 MHz. (see Tsien and Waggoner, Fluorophores for Confocal Microscopy, in Handbook of Confocal Microscopy, James B. Pawley, ed., Plenum, N.Y., 1990).

The recently developed cyanine dye, Cy5, has been reported to be easily conjugated to antibodies, avidin, DNA and other molecules important in fluorescence biomicroscopy and, in addition, possesses the desirable qualities of a high quantum efficiency, stability and long wavelength excitation (Majumdar, et al, Bioconjugate Chem. 4:105 (1993)). The embodiment illustrated in FIG. 7, when outfitted with Ti-sapphire lasers could excite Cy5 by setting the excitation laser 70 at the 680 nm low wavelength end of the laser's tuning range, and quench by setting laser 71 at about 740 nm. The coumarin dyes are commercially available conjugated to molecules useful in fluorescence microscopy (Molecular Probes, Inc. Eugene, Oreg.), and have the advantage of a large Stokes shift to minimize unwanted fluorescence excitation by the quenching beam. Furthermore they have a large stimulated emission cross section, as evidenced by their widespread use in dye lasers, and they also have been successfully used in two-photon excitation microscopy (Denk et al, Science 248:78 (1990)). The dye coumarin 1 (7-diethylamine-4-methylcoumarin) can be excited by two photon excitation by a Ti-sapphire laser set to about 700 nm. Quenching can be by the frequency doubled 950 nm output of the Ti-sapphire laser, to produce pulses at 475 nm. The widely used dye, Lucifer Yellow, has the advantage of a very large Stokes shift, and can be two-photon excited by the output of a Ti-sapphire laser at 850 nm or single photon excited by the frequency doubled 850 nm output (i.e., 425 nm), and the quenching beam can be the frequency doubled 1080 nm output of the Ti-sapphire laser (i.e., at 540 nm). Because of lucifer yellow's large Stokes shift, it is possible to quench by tuning the quenching laser in the optimum of the emission band, which is also at the long wavelength cutoff region of the frequency doubled Ti-sapphire laser. It may desirable to lengthen the pulse width for the quenching beam to, say, 10 picoseconds, both to eliminate two-photon fluorescence excitation in the UV portion of the Lucifer Yellow excitation spectrum, and also to sharpen the spectral spread so that a narrow band rejection beam filter 27 can eliminate unwanted direct and scattered light from the quenching laser from adding noise to the fluorescence signal recorded by the photodetector 23. Alternatively, or in addition to spectral filtering of this direct and scattered quenching laser light, the output of detector 23 can be gated to be unresponsive during the time such direct scattered light from the quenching laser is falling on it. Yet another means to reduce quenching beam photons from reaching detector 23 is to replace dichroic beam splitter 15 with a polarizing beam splitter which reflects plane polarized light from lasers 70 and 71 and transmits the opposite plane of polarization. To the extent that the fluorescent emission is depolarized it will be able to be partially transmitted through the polarizing beam splitter. (In case the fluorescent emission is polarized, a quarter wave plate between the polarizing beam splitter 15 and the specimen will rotate the plane of polarization by 90 degrees, so it will pass through the beam splitter and reach the detector.)

These examples of fluorescent dyes have been discussed principally because they can be excited and quenched with the wavelengths available from Ti-sapphire lasers, which unfortunately have a wavelength gap from about 540 nm to about 680 nm, which is in the region of excitation or quenching of some dyes which otherwise would be good candidates for the present invention. The use of optical parametric oscillators, or lasers able to operate within this wavelength gap of the Ti-sapphire laser, will permit the use of such dyes. A particularly promising class of dye for use in the present invention are the inclusion compounds of the cyclodextrin molecule and various laser dyes occupying its hydrophobic central cavity. The extensive search for laser dyes has found dyes which in many aspect are ideal for the present invention, having a high quantum efficiency, a high stimulated emission cross section and a low ground state absorption at the wavelength of stimulated emission. The use of a cyclodextrin host allows hydrophobic dyes which ordinarily are not suitable for aqueous environments to operate in a hydrophobic microenvironment within an aqueous environment.

In the embodiments described so far, the mechanism focusing laser light on annular aperture 21 insures that the light leaves this aperture generally coherently and in-phase. However such illumination is not optimal for reducing the width of the central minimum. The reason is that, starting from a point on the first minimum ring of an Airy disc pattern, movement towards the central maximum or movement away from it (towards the first bright ring of the Airy disc) both lead to an increase intensity, however in the two directions the oscillating electric field vector of the light is opposite. The problem this opposite electric field causes may be seen by considering just the contribution of two small segments of aperture 21 on opposite sides from the center. Each of these segments projects its own Airy disc in the specimen, positioned so that the first dark ring of both of these Airy discs passes through the central minimum. However a small distance from the central minimum, the area between the central maximum of one of the Airy discs and the common central minimum coincides with the area between the central minimum and the first bright ring of the second Airy disc. Since the two light sources are coherent and in phase, these areas will have opposite electrical vectors, and therefore there will be destructive interference. The result of this cancellation is that the net light intensity grows relatively slowly with distance from the central minimum. One solution to this problem is to employ as quenching laser 11 or 71, a laser with inherently low coherency. The excimer laser has the right coherency properties, but unfortunately is a pulsed laser with too low a frequency to be practical in a scanned laser device such as the device of FIG. 1, however it might be usable in the more parallel embodiments of the invention.

FIG. 8 shows a solution to this problem an embodiment of the invention where diametrically opposite sources of quenching light, which are positioned so as to summate in the specimen to create the central minimum, produce light which is 180 degrees out-of-phase. Therefore in the areas near the central minimum, light from the two sources will constructively interfere, causing the intensity to rise sharply with distance from the central minimum, thereby decreasing the width of the central minimum. Measured in the plane of focus, the sharpening due to just two out-of-phase sources is in just one dimension. Unfortunately to try to extend each source into a semicircle, so that together they encompass the entire annular aperture, will still produce a central minimum in which only one dimension is narrowed by the process. However in arraying two or more pairs of out-of-phase sources at the corners of a regular polygon, such that coherence between different pairs is minimized, will solve the problem by approximating a radially symmetrical central minimum, narrow in two orthogonal dimensions.

In the device of FIG. 8, the annular aperture 21 of FIG. 1 is replaced by a hexagon of illuminated optical fibers. Light from excitation laser 10 is focused by lens 12 onto one end of optical fiber 91, and light emerging from the other end 98 of fiber 91 is reflected from dichroic mirror 14, and directed through beam scanning means 16 to lens 18, which focuses this excitation light to a spot on the specimen 19. Three lasers 11, 11' and 11", each within the band of effective quenching, but of wavelengths far enough from each other that they are mutually incoherent, have their output beams focused by lenses 92, 92' and 92" onto three pairs of phase preserving optical fibers, one pair containing fibers 94 and 95 being illustrated along their full length. The non-illuminated ends of these fibers, for example end 96 and 97, are in the plane 99, that is conjugate to the plane of focus of specimen 19, and consequently is the same plane occupied by annular aperture 21 in FIG. 1. By mechanically adjusting fiber end 96 with respect to fiber end 97 (the means for such adjustment is not illustrated) the quenching light emerging from these ends on plane 99 is 180 degrees out-of-phase. As shown in FIG. 9, which shows a cross section through plane 99, the ends 96 and 97 are at diametrically opposite vertices of a hexagon, and the separation between ends 96 and 97 is such that at the wavelength of laser 11, the Airy discs of these fiber ends projected into the specimen have their first minima passing through the central point of the central maximum of the Airy disc projected by lens 18 on the specimen 19 from light emerging from the end 98 of fiber 91. Dichroic mirror 14 makes the end 98 of fiber 91, conducting excitation light, conjugate to the central point of the hexagon of non-illuminated ends 96, 96', 96", 97, 97', and 97", but it is also possible to locate the end 98 physically within that hexagon, so that dichroic mirror 14 is unnecessary. (FIG. 8, it will be realized has described just the system for illuminating the specimen, and the viewing system, using a dichroic mirror, is the same as in other embodiments.)

Another way to provide the necessary incoherence between the various pairs of out-of-phase sources, is for them to have the same wavelength, but to be on at different times, so that interference is impossible between one pair and another pair. The device of FIG. 10, which is the preferred microscope embodiment of the present invention, uses a pulsed laser 71 directed by lens 92 into four phase-preserving optical fibers 100, 101, 102 and 103 (six or any even number of fibers greater than two could have been used instead of four), so that a single coherent pulse simultaneously enters all four fibers. (Though these four fibers have been shown receiving the focused beam from laser 71 arranged in a line, more likely they would be arrayed in a compact square, or the laser would be directed into just one fiber, the output of which would be split twice by well known methods in the art of fiber optics.) Two of the fibers 100 and 101 are short, and have a difference in length of one half the wavelength of the laser light, in order to make their outputs out-of-phase. (Or they have the same length and the phase difference is adjusted by mechanically adjusting their ends,) The two remaining fibers 102 and 103 (illustrated for just part of their lengths) are long (also with a small difference in length to insure that their output is out-of-phase), and their length is such that by the time the light pulse emerges from them, the light has stopped exiting the short fibers (that is to say that the length difference between the short and the long fibers is equal or greater than the laser pulse duration times the speed of light). The exciting light from laser 70 emerges from the end 98 of fiber 91, end 98 being in the center of the square formed by the non-illuminated ends 104 to 107 of the fibers 100 to 103. A diagram of the ends of the fibers through the plane of these ends is shown in FIG. 11.

Figure 10:
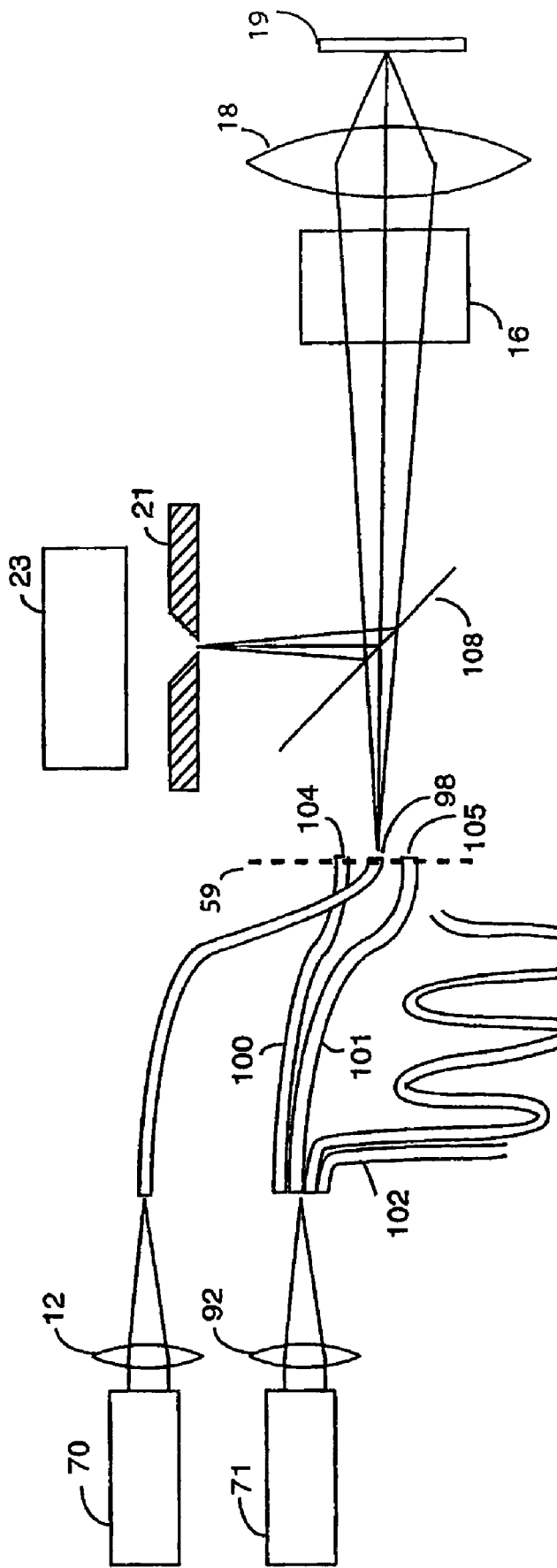
FIG. 10 is a schematic cross-sectional view of an embodiment of the present invention combining the features of the devices illustrated in FIGS. 7 and 8.
Figure 11:
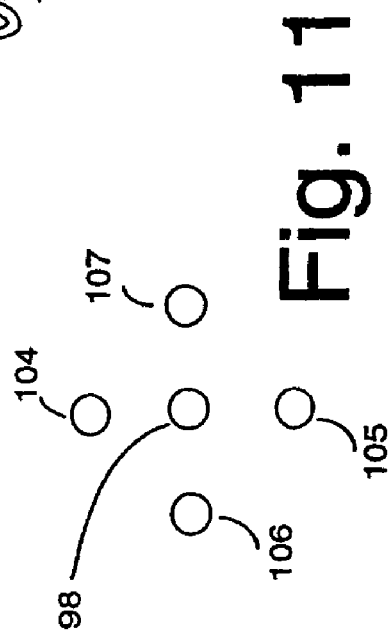
FIG. 11 is a diagram showing the arrangement of the non-illuminated ends of the fibers in the device of FIG. 10.

As in the embodiment of the invention shown in FIG. 7 excitation laser 70 of FIG. 10 emits a pulse first, followed by quenching laser 71. The fluorescent emission from the specimen is reflected by dichroic mirror 108 then passes through pinhole 22 onto a photodetector 23, the output of which modulates either the spot of a display cathode ray tube, raster scanned in synchrony with the scanning of the superimposed excitation and quenching beams across specimen 19, by scanning means 16, or scans the write address in an image frame store. As in earlier embodiments, there is assumed to be a blocking filter (unillustrated) in front of the detector 23, to eliminate both excitation and quenching photons from entering the detector, and furthermore, the detector may be time gated to be insensitive during the times the excitation and quenching lasers are on, and their light may be directly reflected back by the specimen. The convex lens 18 here symbolizes the complex imaging optics of a compound microscope, which may include in addition to an objective, an eyepiece lens and perhaps other lenses and other optical elements as well.

Figure 12:
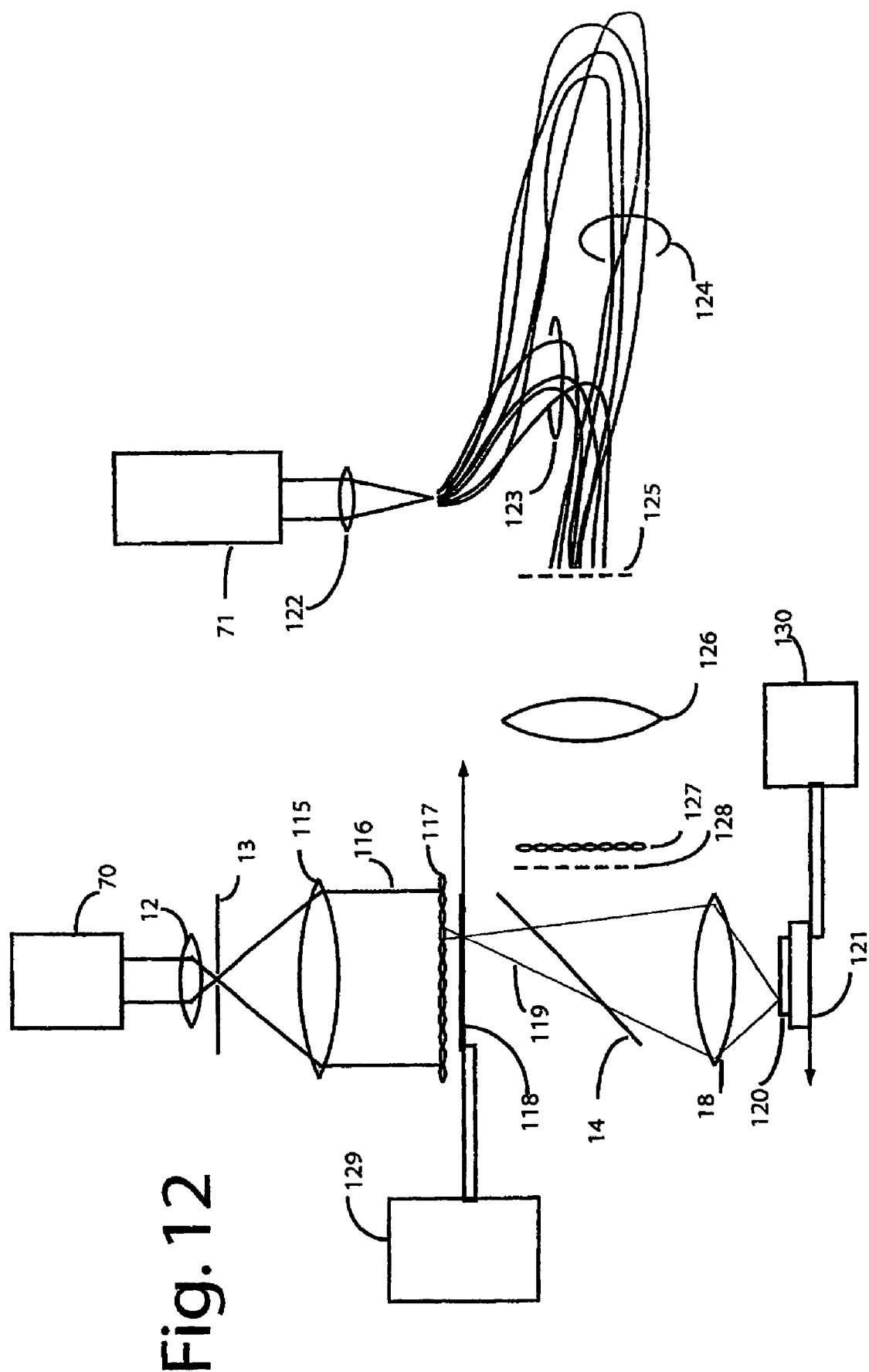
FIG. 12 is a schematic cross-sectional view of an embodiment of the present invention applied to microlithography.

FIG. 12 shows the form of the present invention adapted to the field of photolithography, which enjoys the benefits of quench sharpening, while at the same time applying an image to the wafer with massive parallelism, to achieve a high throughput. When the present invention is adapted to microlithography, the excitation laser excites a photoactive molecule in a photoresist layer of a wafer to be made into microchips. The photoactive molecule then enters a transient excited state analogous to the excited state of a fluorescent molecule, which at least in many cases should be susceptible to optical quenching, though the period of vulnerability of the state to quenching is far shorter than the case of the fluorescent molecule. When quenched the photoactive molecule reverts to its ground state. However if not quenched it has a probability of causing a lasting change, constituting the "latent image," which will change the vulnerability of the photoresist layer to some development process, where for example exposed areas become insoluble and remain on the wafer, protecting it, while non-exposed areas can wash away, leaving parts of the wafer vulnerable to some etching process.

Figure 13:
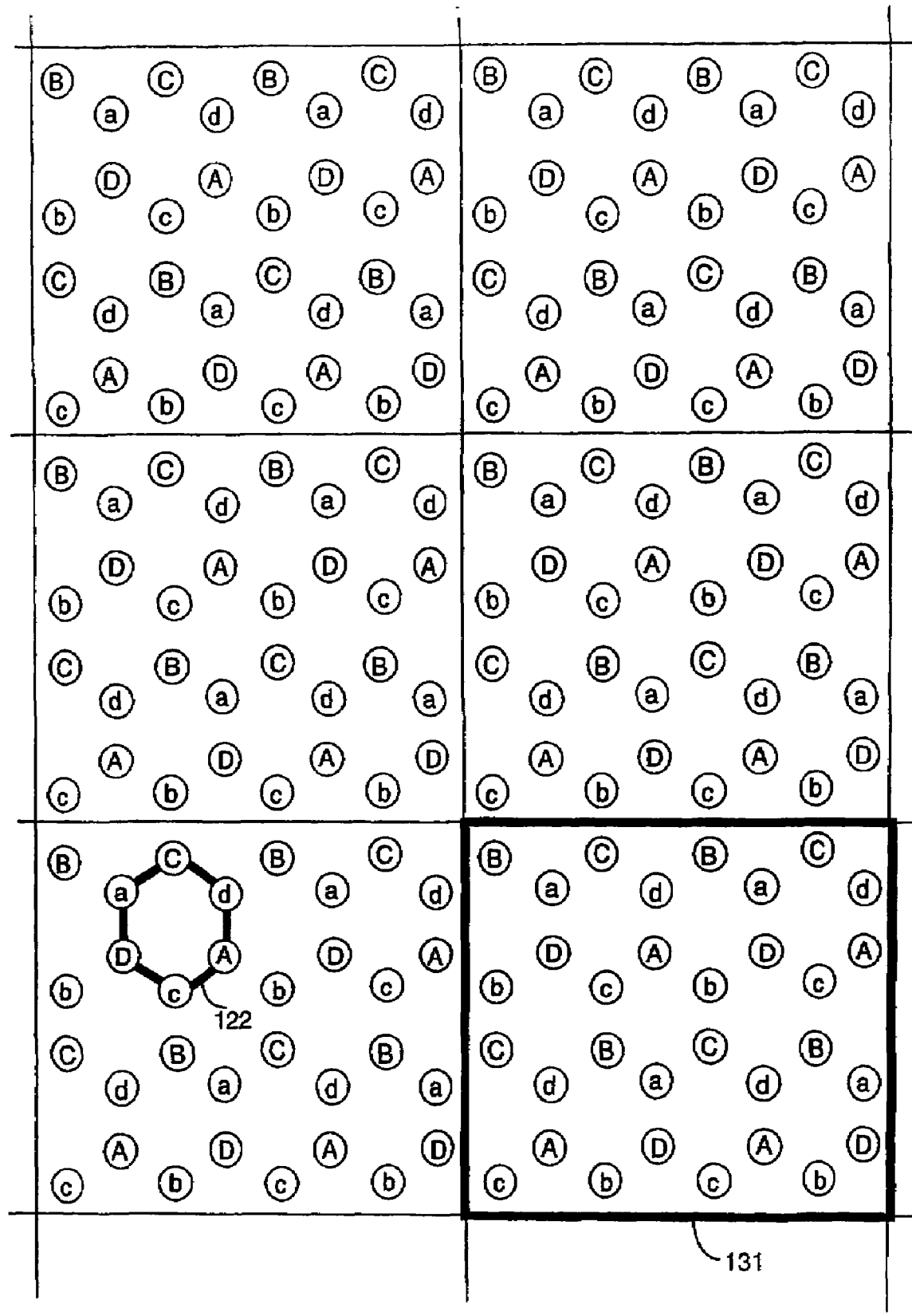
FIG. 13 is diagram showing the ends of the quenching beam optical fibers in the device of FIG. 12, in the plane conjugate to the photoresist layer.

In the microlithographic embodiment, excitation pulsed laser 70 is focused by lens 12 to a pinhole 13 and the beam emerging from pinhole 13 is collimated by lens 115 and the emerging plane wave 116 is directed on microlens array 117, which projects focused spots from laser 70 on a projection mask 118. The lenses of microlens array 117 are arranged in a regular hexagonal array, so that the spots projected onto mask 118 are at the centers of the hexagons of such an array. Where a spot of excitation light is imaged by any of the microlenses on a transparent region of mask 118, the light emerging for example ray cone 119, passes through dichroic beam splitter 14, and is focused by lens 18 to the photoresist layer 120 on wafer 121. Because array 117 can simultaneously focus thousands of spots, an image can be transferred from the mask 118 to the photoresist layer 120 on wafer 121 with an enormous degree of parallelism. Light from ultrafast pulsed quenching laser 71 (synchronized with laser 70 as described above) is imaged by lens 122 onto a bundle of 32 phase preserving optical fibers, arranged into four bundles of eight fibers each, two bundles 123 and 124 of which are illustrated, each with only four out of the eight fibers, to simplify the illustration. Each bundle has a different length, so that the pulses from the laser emerge at different times from each of the bundles, and therefore light emerging from fibers in one of the bundles cannot interfere with light emerging from another bundle. The rectangle 131 in the lower right corner of FIG. 13 shows the ends of each of the 32 fibers in the plane 125 of FIG. 12. The fibers in bundle 123 are schematically shown in rectangle 131 as circles with either a lower case "a" or a capital "A," those in the lower case "a" having light which emerges 180 degrees out-of-phase with respect to light emerging from the circles with capital "A." (Note that the diameters of the circles in FIG. 13 are not drawn to scale, in relationship to the dimensions of the hexagons.) Similarly, fibers in bundle 124 terminate in the circles with a lower case "b" or a capital "B." with a similar out-of-phase relationship between the lower case "b" and the capital "B" fibers, and so on for the unillustrated fibers ending in the circles with c's and d's. Light emerging from the unilluminated ends of the fibers terminating in plane 125 (which has been drawn separated from the ends of the fibers for clarity, but is actually assumed to be in the same plane with these ends), is focused to infinity by lens 126, and the light passing through lens 126 is directed onto microlens array 127, which is a rectangular array with the same aspect ratio shown in FIG. 13, and which is of the appropriate lens spacing to image the ends of the fibers at plane 125 to the repeating hexagonal pattern at plane 128 shown in FIG. 12. (One typical hexagon is labeled 132 in FIG. 13.) The scale of the pattern at plane 128 of the focused images of the fibers at plane 125 is such that when the light leaving plane 128 is reflected from dichroic mirror 14, and imaged by lens 18 onto the photoresist layer 120, there is an image of each spot from the plane of the mask 118, where the mask is transparent, projected into the center of one of the hexagons of the array of fibers conducting the quenching radiation. It should be noted that each hexagon has the same coherency and phase relationship as the device shown in FIGS. 8 and 9, namely quenching light imaged on opposite sides of the hexagon is coherent and 180 degrees out-of-phase while light imaged on adjacent vertices is mutually incoherent, in this case because the imaging occurs at different times due to the different time delays in the different fiber bundles such as bundle 123 and 124. It is assumed that the pulses from the lasers 70 and 71 are short enough, e.g., some hundreds of femtoseconds or less, that it is possible to have four different delays for the fiber bundles conducting the quenching light, so that quenching still arrives at the photoresist layer 120 before the excited state induced in the photoactive molecules by the light pulse from laser 70 has decayed either to a non-quenchable triplet excited state, or has initiated the latent image local chemical change. Therefore, provided sufficient accuracy can be provided in the fabrication of the two microlens arrays 117 and 127, and the relative phases can be maintained through the successive imaging steps for the quenching radiation, the projection in the photoresist of each hexagon provides satisfactory quench sharpening for the spot of excitation in its center.

The array of spots projected onto the photoresist layer 120 is converted into a continuous two dimensional image of the mask 118 by laterally translating the mask by motor means 129 and laterally translating the wafer 121 in opposite direction by motor means 130, with a ratio of velocities equal to the magnification of lens 18, so that during scanning, the image of mask 118 maintains a stable relationship with the photoresist layer.

Figure 14:
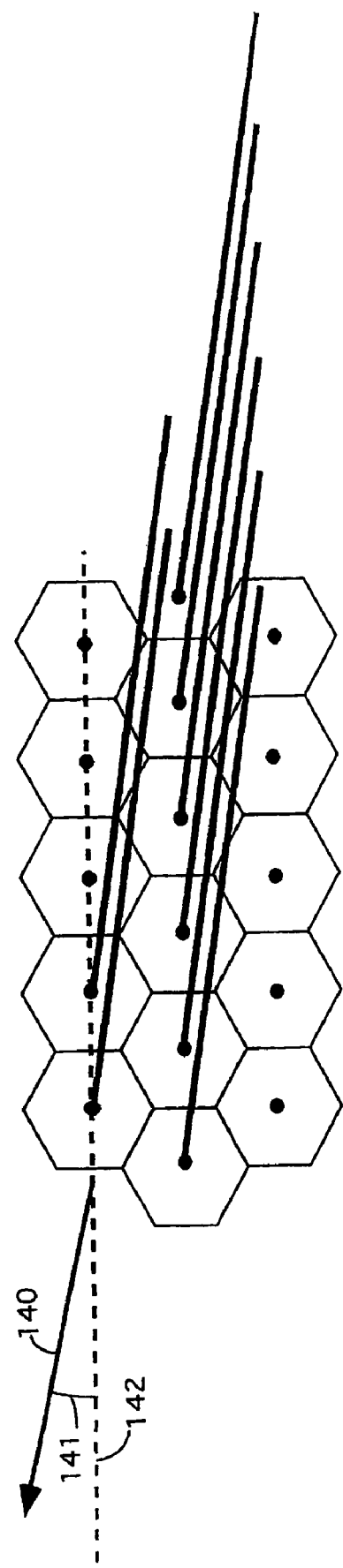
FIG. 14 is a diagram showing the direction of translation of the mask in the device of FIG. 12.

As shown diagrammatically in FIG. 14, the direction of translation of the mask (shown by arrow 140) is such that it is at a small angle 141 with respect to one of the major axes 142 of the hexagonal array of excitation spots projected by microlens array 117, so that the trajectory of two adjacent spots in the array form two parallel lines separated by less than the post-quenching resolution distance when referred to the photoresist layer, and such that by the time the entire mask has been scanned in front of the microlens array 117, the trajectories of all the excitation spots form a continuous grating pattern on the photoresist, with no gaps or regions of overlap. As is evident from FIG. 14, the angle 141 would be much smaller as the number of hexagons per row is increased from the five in the figure, to perhaps a thousand or more, as imagined for the device of FIG. 12. It is also possible to have an angle 141 which is a small multiple of the angle required for no overlap, in order to have the same point on the resist exposed by different sets of excitation/quenching microlens combinations, so that any defects in a particular microlens can be compensated by proper exposure from another microlens.

Unlike the apparatus shown in FIGS. 8 and 9, where only the contributions from six points must be considered when computing the shape of the central minimum for the quenching beam on the photoresist, in an array such as in the embodiment of FIG. 12, contributions from farther points must also be considered. Fortunately, in the case of a hexagonal array, neither the six send nearest neighboring points, nor the 12 third nearest neighboring points contribute substantially to the intensity at the central point of the central minima, because at their particular distances, they are near minima in the Airy disc distribution. Interestingly this is not the case for square arrays. However, even in square arrays, when diagonally opposite points are out-of-phase, then for each central minimum, the contribution from the higher order points always cancels.

An additional advantage of creating the central minimum of quenching radiation by superposition of out-of-phase sources, is that the two opposite sources can be closer than when zero central intensity is produced by over lap of first minima of in-phase or mutually incoherent component sources. In theory, with out-of-phase sources, the central point will have zero intensity for all distances between the opposite sources but when too close the peak power in the specimen is severely reduced. An ideal spacing appears to be about half the spacing from each other dictated by the requirement to overlap first minima of the component Airy discs or in other words, the image in the specimen of the central maximum of one of the two out-of-phase sources coincides with the first dark Airy disc ring of the other source. Compared to the spacing where the dark rings coincide, such reduced spacing yields about doubling of effective resolution for a given exposure of the specimen to quenching beam power. Finally, because of the relative tolerance of resolution to variations in intersource spacing, the sources can have a larger area than with the requirement of superposition of first dark rings.

As the technology for making large matrices of shutters evolves, it would probably be preferable to implement the technology of the parallel device of FIG. 12, by having the information about mask 118 encoded in a digital memory, which would be read out with massive parallelism to a shutter array positioned at the plane of the mask 118, so there would be no need to move the mask.

It is therefore believed that the present invention, and in particular the preferred microlithography embodiment shown in FIG. 12, may allow microchips of exceedingly fine critical dimensions to be fabricated economically, for the most part, using tool and processing components currently in place at chip fabricating facilities. Because these chips would not have to be exposed to ionizing radiation in the exposure of the photo resist annealing steps required in chip manufacturing processes requiring ionizing radiation could be eliminated, and the resulting absence of any defects which might escape the annealing process would lead to chips of greater reliability.

Figure 15:
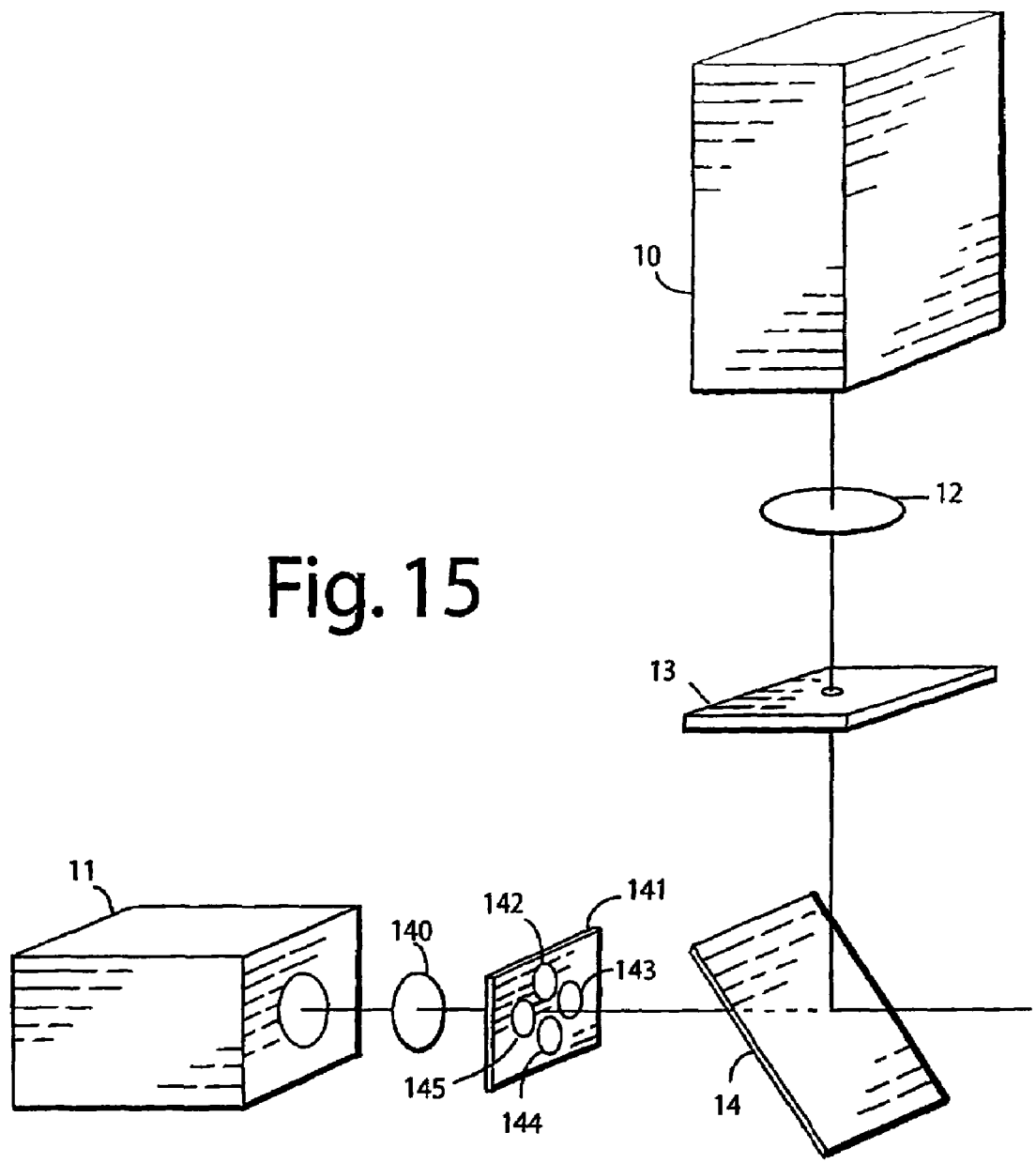
FIG. 15 is a perspective view showing a detail from an alternative embodiment to the device of FIG. 1, where the pattern of quenching radiation is produced by passing the quenching light through a filter having regions of differing phase shifts.
Figure 16:
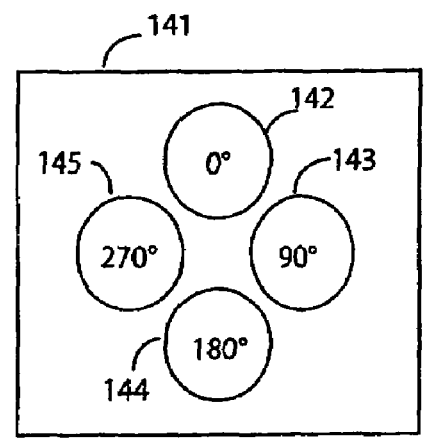
FIG. 16 is a enlarged view of the filter in the device of FIG. 15, showing the phase shifts for various regions.

In the embodiments of the present invention shown in FIGS. 8, 10 and 12, the requirement that different pairs of out-of-phase sources not optically interfere with other pairs was met 1) by making the pairs have different wavelengths or 2) by having light emitted in pulses that did not overlap in time. FIG. 15 shows how the device of FIG. 1 can be modified to have the advantages of out-of-phase sources without requiring separate lasers for different pairs, or requiring optical fiber delay lines. Quenching light from pulsed laser 11 is focused by lens 140 onto an opaque filter 141 with 4 transparent openings 142, 143, 144 and 145, containing optical delay plates, delaying the light by 0°, 90°, 180° and 270°, respectively). FIG. 16 shows a magnified view of the filter 141. The elements in FIG. 15 are assumed to be part of a modification of the device shown in FIG. 1, so that the quenching light leaving filter 141 pass through dichroic beam splitter 14 and then via elements 15, 16, 17, and 18 are directed to the specimen 19, as shown in FIG. 1. (As described earlier, far better performance is expected when the lasers are pulsed lasers, but to reduce confusion, the continuous wave lasers 10 and 11 of FIG. 1 have been shown in this example.)

With respect to interference, two sources of mutually coherent light with a 90° phase difference act substantially like mutually incoherent sources. Therefore the quenching light leaving openings 142 and 144 will act as if it is incoherent with respect to the light leaving openings 143 and 145, and thus the image in the specimen of openings 142, 143, 144 and 145 will be similar to the image in the specimen of fiber ends 104, 107, 105 and 106 of the device of FIG. 10. Thus by replacing the toroidal lens 22 and the annular aperture 21 of FIG. 1 with the lens 140 and the filter 141 of FIG. 15, a substantial improvement in resolution is gained.

Figure 17:
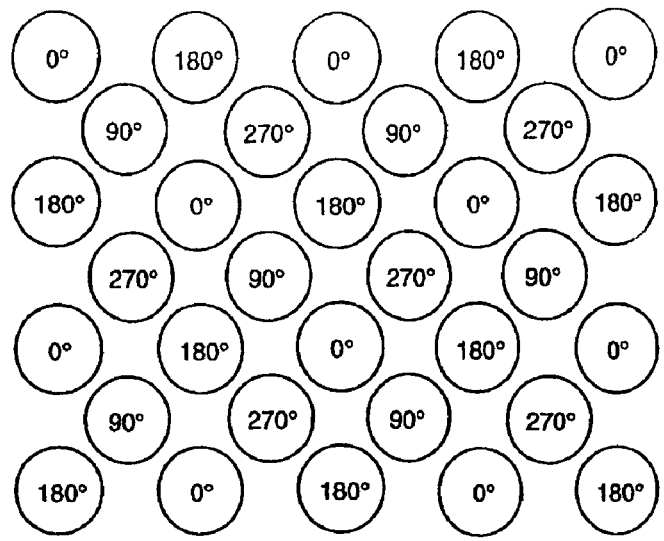
FIG. 17 is view of a filter having regions of different phase shifts arranged in a square matrix.

The use of 90° and 270° phase shifts to produce non-interference can easily be generalized to the devices of FIG. 12, where multiple points are simultaneously resolution enhanced. However, a square rather than hexagonal matrix is required. FIG. 17 shows such a matrix, where the phase shifts within each of the circles is shown, and where the space outside the circles is opaque. Such a matrix filter could be produced for millions of simultaneously illuminated points, using the well known techniques for producing phase shifting masks for the microlithographic industry. The matrix shown in FIG. 18 adds intermediate phase shifts at 45°, 135°, 225° and 315° to make the shape of the resolution enhanced spot profile more closely approach a circle, when this is desired. One immediate advantage of use of a matrix of illuminated points, is that each projected spot of quenching radiation in the specimen services four rather than one excitation spot, so in cases when the resolution achievable is limited by the ability of the specimen to tolerate high powers of quenching radiation, use of simultaneous multiple excited points may result in improved resolution.

Figure 18:
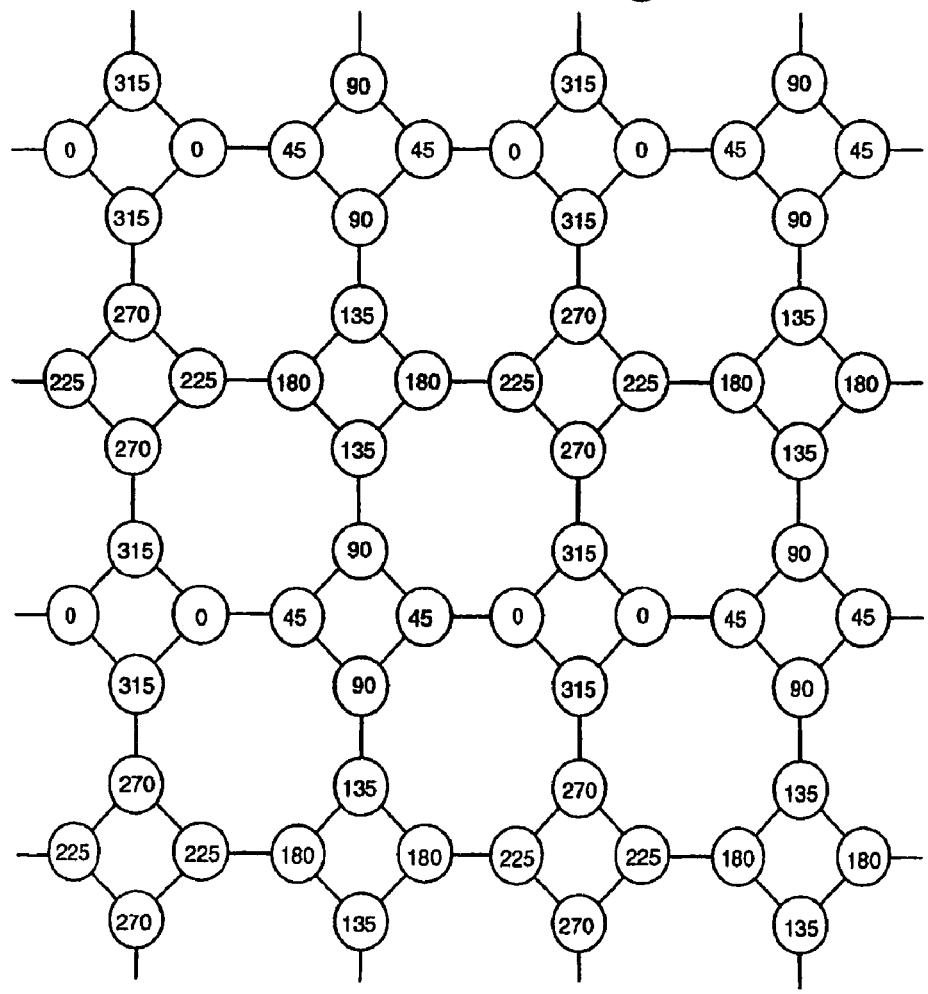
FIG. 18 is view showing a filter showing regions with eight distinct phase shifts, arrayed in a square matrix.
Figure 19:
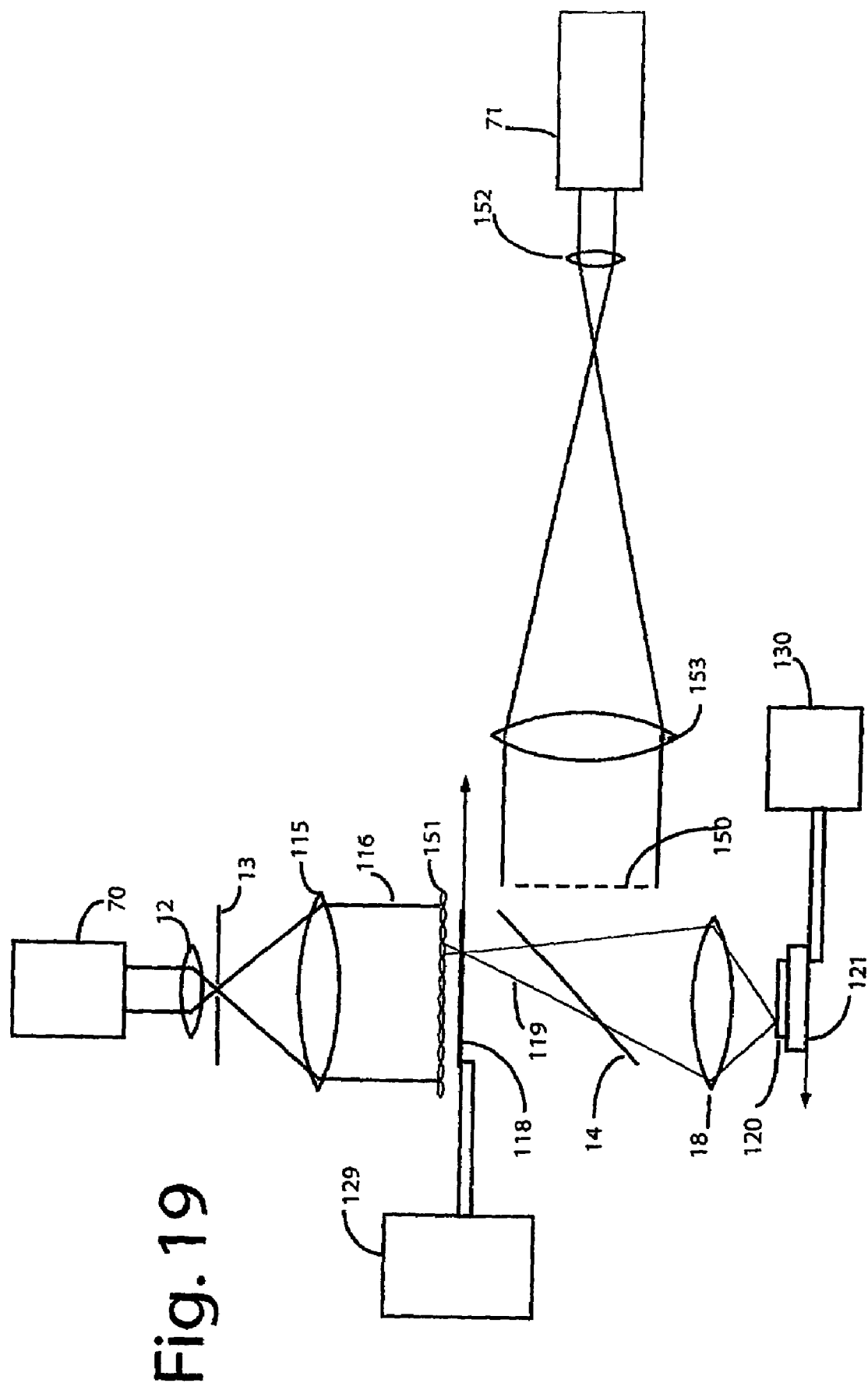
FIG. 19 is a schematic cross sectional view showing a microlithographic embodiment of the present invention, where the pattern of quenching radiation is produced by a matrix similar to that shown in FIG. 17.

FIG. 19 shows a modification of the device of FIG. 12, using a phase shifting matrix as shown in FIG. 17 or FIG. 18. This matrix filter 150 is located at the plane which is conjugate to mask 118 with respect to dichroic mirror 14. The microlens array 151 is a square rather than the hexagonal array 117 of FIG. 12, but works in the same way. Filter 150 is illuminated by pulsed quenching laser 71, the output beam of which is expanded by lenses 152 and 153. Filter 150 is positioned, and the scale of its openings are such, that the central minima of quenching light emanating from filter 150, projected onto the photoresist layer 120, coincide with the central maxima of light passing through the microlenses in array 117, which because they pass through a currently transparent part of mask 118, reach the photoresist layer 121. The synchronized translation of the photoresist layer 120 and the mask 118 are as described for the device of FIG. 12. It will be appreciated that the device of FIG. 19 is simpler than the corresponding device of FIG. 12, but there is a possible problem in case the required brevity of the pulses from laser 71 causes a spectral broadening.

When a phase retarding element has zero chromatic dispersion, then the two wavelengths will be retarded by the same time interval, not the same phase. This means that if the element produces a 180° phase shift for one of the wavelengths, in general the phase shift for the remaining component will not be 108°. In devices such as that in FIG. 19 those wavelengths which are not exactly out-of-phase will increase the intensity of light at the central minima of quenching light, reducing the efficiency of the device. Optical fibers have been developed with a high negative chromatic dispersion, meaning that long wavelengths travel slightly slower through the fiber than shorter wavelengths. If fiber 100 in the device of FIG. 10 were an appropriate length of such a fiber, and fiber 101 were a zero chromatic dispersion fiber, it should be possible, over a range of wavelengths, to make each wavelength emerging from fiber ends 104 and 105 have a phase difference of 180°. Such a scheme could be applied to the microlithographic embodiment of FIG. 12 more simply than to that of FIG. 19.

Figure 20:
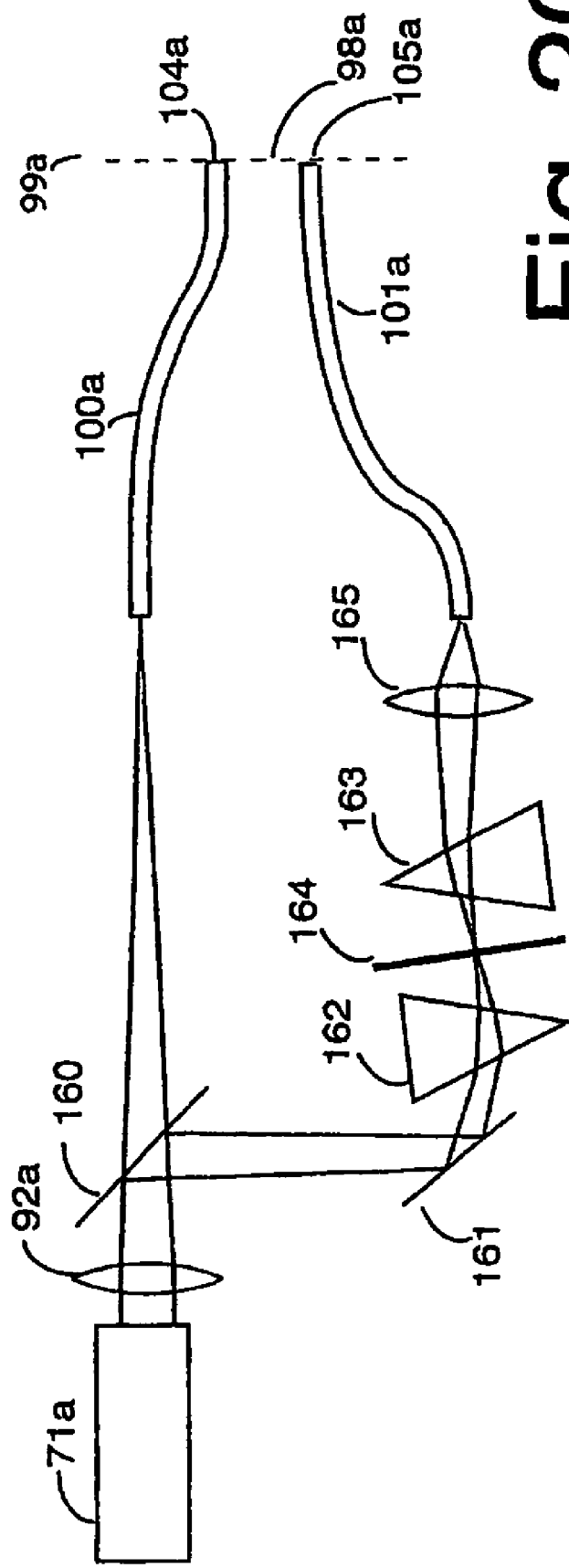
FIG. 20 is a schematic cross sectional view showing how a dispersion compensating assembly can allow production of sources of quenching radiation where all the wavelength components have the same 180° phase shift.

FIG. 20 schematically shows an alternative solution to maintaining an out-of-phase relationship over a range of wavelengths. Fibers 100a and 101a in FIG. 20 correspond to fibers 100 and 101 in FIG. 10, and other corresponding elements have also been labeled with the suffix "a". Instead of illuminating the fibers by the same focused laser as in FIG. 10, a beamsplitter 160 creates a pair of beams from the laser output, one which is directly focused on the lit end of fiber 100a and the other of which, after reflection by mirror 161, is passed through a chromatic phase compensating assembly, consisting of prisms 162 and 143 and a phase retarding filter 164 at the chromatically dispersed focus of the laser beam, between 162 and 163. Prism 163 reassembles the spectral components into a single beam, which is then focused by lens 165 on the lit end of fiber 101a. Because each spectral component is focused to a particular spot on filter 163, by adjusting the thickness of the filter at that point particularly for the component, each component can be separately adjusted to be exactly 180° out-of-phase at plane 99a. With this arrangement, any dispersion within the fibers 100a and 101a can also be compensated. It will be appreciated that there is probably no need in this device for a literal filter 164, but by suitably tilting the apparatus, the phase shift can be changed as a function of wavelength. It will also be appreciated that for the prism 163 to efficiently undisperse the light dispersed by prism 162 some focusing means should be included between the prisms. However such optical devices in which a beam of light is first dispersed and then undispersed, are so widespread in the art, for example for pulse stretching and compression for ultrafast lasers, that this schematic in FIG. 20 will be sufficient. Needless to say, when a chromatic phase compensating device, or negative dispersion optical fiber must be used to provide a constant phase shift over a spectral region, the device such as shown in FIG. 12 is more appropriate than that shown in FIG. 19. To enjoy the benefits of the simplicity of the device of FIG. 19 in the field of microlithography, it might be necessary to develop photoresists with unusually long lifetimes for the optically quenchable excited state, enabling quenching pulses to be long enough to approach monochromaticity.

Figure 21:
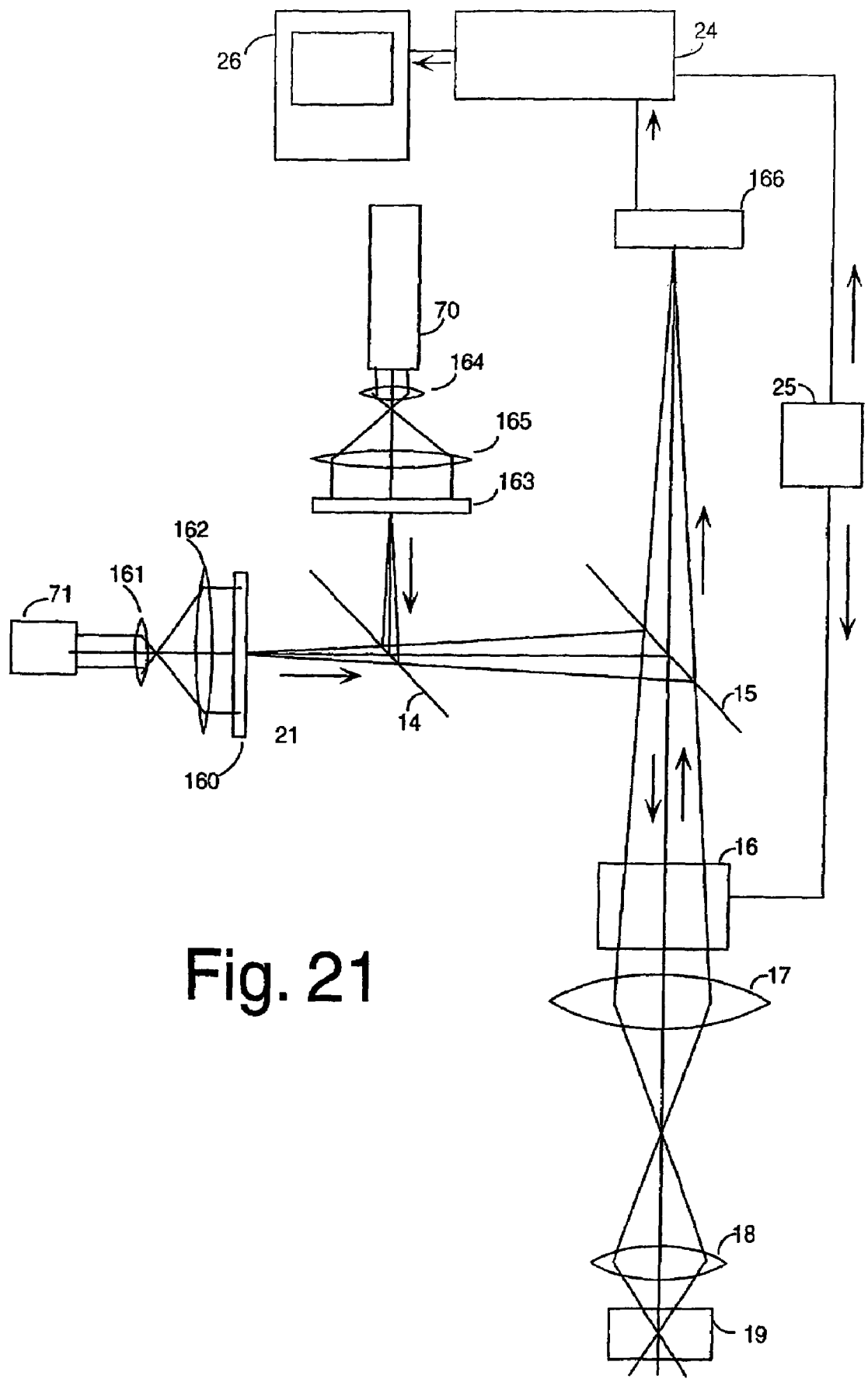
FIG. 21 is a schematic cross sectional view showing a form of microscope embodiment of the present invention, where many points are simultaneously viewed.

In microscopic applications of the present invention, on the other hand, the quenchable state fluorescent lifetime is already, usually, more than hundreds of picoseconds, so the quenching pulse can be long enough to approach monochromaticity. FIG. 21 illustrates a microscope which uses a phase shifting filter such as shown in FIG. 17 to achieve massive parallelism in exposure, allowing rapid frame rates to be coupled with high pixel count images with extraordinary resolution This microscope is adapted from the device of FIG. 7, and elements with the same numbers as in the former figure are explained in the text for that figure. Elements to synchronize the lasers, shown in FIG. 7, have not been repeated in FIG. 20 for simplicity, as have other elements with obviously similar functions. Replacing the annular aperture 21 of FIG. 7 is an elongated square matrix filter 160 similar to that shown in FIG. 17, but with about 200 squares in the long dimension and 20 squares in the short dimension. Matrix filter 160 is oriented in the FIG. 20 so its long dimension is vertical. Matrix filter 160 is illuminated by pulsed laser 71, the output beam of which is expanded by lenses 161 and 162 (which may be cylindrical) to uniformly illuminate filter 160. Pinhole array 163 has pinholes in a square array, positioned so that the mirror image of the pinholes with respect to dichroic beamsplitter 14 coincide with the centers of the squares of the matrix filter 160. This arrangement insures that the central maxima in the specimen 19 from the pinholes in array 163, as illuminated by the beam expanded excitation laser 70, will coincide with the central minima produced by the quenching light emitted from matrix filter 160. Lenses 164 and 165 perform the beam expansion for laser 70. Beam deflector 16, which has only to deflect the beam in one dimension so that the coincident images of the elongated filter 160 and array 163 moves in the direction of their short axis. More accurately the axis of movement is at a slight angle with respect to the short axis, so that as the scanning by deflector 16 takes place, the coincident excitation maxima and quenching minima traverse paths similar to that shown in FIG. 14. Each of the illuminated spots in the specimen 19 is imaged on a separate light detector in detector array 166, which ideally would have detectors such as avalanche photodiodes which approach the sensitivity of photomultiplier tubes. For each position of deflector 16, each detector in array 166 is receiving light from a unique position (x, y) in the specimen. During scanning the output of array 166 is directed to a frame store memory, along with a scan position signal from scan drive circuit 25, so that the output for each detector in array 163 can be directed to the appropriate location in the frame memory. The frame memory is raster scanned continuously to produce an image of the specimen on monitor 26. Because lateral scanning is required in just one dimension, a fast scan rate is possible, which should allow real-time 3-D reconstruction of the specimen, by adding a depth scan. Although the device of FIG. 10 is preferred in terms of fitting into the mainstream of point scanned microscopes, the embodiment shown in FIG. 21 may have advantages in many applications, where its imaging speed, resolution and possibility of real time 3-D reconstruction may be useful.

For most microscopy and microlithography applications of the present invention, while it is desirable to restrict spot area as much as possible in the lateral dimension, in the depth dimension, a high depth of field is preferred. For example in microlithography, combining a narrow lateral spot size with an elongated longitudinal spot, to make a needle like exposed area, would allow the process to tolerate field curvature of the objective, and would also allow the full depth of the photoresist to participate in responding to the light. This would also insure that the walls of the features etched in the resist have walls with a profile perpendicular to the surface. In the case of microscopy, a needle shaped area of excitation would produce the equivalent of the confocal microscope technique of summation of many sections at different depths, only the required specimen exposure would be just that for a single section. Fortunately, the shape of the effectively exposed area, when quenching is produced by devices such as shown in FIG. 8 or 10 has this very elongated shape.

It is possible to produce even more longitudinally elongated, needle-shaped areas of sharp focus, by modifying the device of FIG. 8, so that instead of six quenching light, such as fibers 94 and 95, there were twelve, with six arrayed in a plane parallel to plane 99, but closer to the beam splitter 14 and six arrayed in a plane parallel to plane 99 but farther from beam splitter 14. The twelve fibers would flash in pairs, but with six flashes rather than the three quenching flashes of the device of FIG. 8, so that there was no interference between the light emitted from different pairs. In this way the area of fluorescent excitation produced by the excitation laser would be chiseled away to a narrow central needle shaped area in six successive steps. Such a result could also be produced by placing an ultraripidly responding variable focusing element in the optical path of the device of FIG. 8, between beam scanner 16 and beamsplitter 14, or at another appropriate place in the optical path, so that after fibers 94, 95, 94', 95', 94", and 95" had their flashes, the focus would be rapidly changed and the same fibers would flash in sequence again, producing the same effect as twelve separate fibers. This same general scheme is also applicable to the microlighographic embodiments such as that in FIG. 12.

There are also times when it is desirable to restrict depth. In these cases, it is possible for the lateral resolution enhancement to be produced by one exposure of quenching light, for example with the arrangement of FIG. 8 or 10, but then within the lifetime of the excited state, expose the specimen to An additional pulse of quenching light produced by the interference of two out-of-phase spots on the optical axis, one above and the other below the central maximum of excitation, thus boxing in the excited area in the depth as well as the lateral dimensions.

The same resolution enhancement techniques described above for microlithography are also applicable to the microfabrication of small parts. Here the ability to manipulate a block of optically writeable material in three dimensions, would allow the production of microminiature parts which may not be available by any other technique, as described in more detail in the parent application of this application, U.S. patent application Ser. No. 08/275,967, now U.S. Pat. No. 5,886,911, and which is incorporated herein by reference.

Similarly the present technique could be invaluable in the optical storage of information, both in the writing and the reading phases of such storage, again as described more fully in U.S. Pat. No. 5,886,911.

While in the embodiments of the present invention described in this specification, both excitation and quenching were carried out by focused beams of light, either or both of these roles might be implemented by focused beams of other types of radiation, for example by X-rays, by focused electron or other particle beams or by focused ultrasonic radiation. In the examples given, the radiationally quenchable excited states have been electronically excited states, however any other types of excited state, including nuclear excited states, excited states involving macroscopic quantum structures, molecular isomerizations, or crystal lattice phenomena, for example, would also fall within the scope of the present invention. In the examples given, focusing of the exciting and quenching radiation is provided by lenses, however other devices for focusing are known, including concave mirrors, tapered light pipes and optical fibers, and these can be used for focusing in the present invention. The examples given have considered a specimen or target material with just one radiationally excitable species, however it is often useful in fluorescent microscopy of biological material to employ two or more contrasting fluorescent stains, and the present invention could be used in such applications, for example by choosing two fluorophores which have the same excitation and quenching wavelengths but differ in fluorescent lifetimes or emission spectra. All the examples given have employed scanning of a spot or line, but the present invention is also applicable to applications requiring selective illumination of just a single unscanned spot. In the examples given, just one point or line in a specimen is scanned at each moment, however it is possible to simultaneously scan multiple points, with the use of Nipkow discs for example, as in the microscope of Petran (U.S. Pat. No. 3,517,980 (1970)) and in such devices, each scanned point is individually subject to the resolution enhancement of the present invention. Thus the scope of the invention should be determined by the appended claims and their legal equivalents, rather than by the examples given.

I claim:

1. An apparatus for irradiating a plurality of selected regions of a target material in order to excite members of an excitable species contained within said selected regions to a particular state of excitation, said apparatus having a plane of focus and comprising: a first source of radiation for generating a first radiation adapted to excite said members to said particular state of excitation; means for directing said first radiation to said plurality of selected regions; a second source of radiation for generating a second radiation adapted to reduce the ratio of excited members in said particular state of excitation to members not in said particular state of excitation at said selected regions; means for directing said second radiation to said regions, so that said second radiation has a minimum portion in each of said regions and means for measuring the radiation emitted from said plurality of selected regions so that radiation from at least two of said plurality of regions is measured simultaneously.

* * * * *